United States Patent
Tanaka et al.

(10) Patent No.: US 10,686,135 B2
(45) Date of Patent: Jun. 16, 2020

(54) COMPOSITION

(71) Applicant: Sumitomo Chemical Company, Limited, Tokyo (JP)

(72) Inventors: Masanobu Tanaka, Tsukuba (JP); Hiroyuki Hayasaka, Osaka (JP); Vaidas Savukynas, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/096,111

(22) PCT Filed: Apr. 4, 2017

(86) PCT No.: PCT/JP2017/014103
§ 371 (c)(1),
(2) Date: Oct. 24, 2018

(87) PCT Pub. No.: WO2017/187906
PCT Pub. Date: Nov. 2, 2017

(65) Prior Publication Data
US 2019/0148639 A1    May 16, 2019

(30) Foreign Application Priority Data

Apr. 25, 2016 (JP) .................................. 2016-087313

(51) Int. Cl.
*H01L 51/00* (2006.01)
*C07C 31/38* (2006.01)
(Continued)

(52) U.S. Cl.
CPC ............ *H01L 51/005* (2013.01); *C07C 31/38* (2013.01); *H01L 51/0007* (2013.01);
(Continued)

(58) Field of Classification Search
CPC .............. G03G 5/14791; G03G 5/0592; H01L 51/0072; H01L 51/0043; H01L 51/50;
(Continued)

(56) References Cited

U.S. PATENT DOCUMENTS 6,894,196 B2 *  5/2005  Okamoto ................ C07C 29/44
568/840
2005/0155632 A1   7/2005  Hayashi et al.
(Continued)

FOREIGN PATENT DOCUMENTS

JP   2004-265672 A   9/2004
JP   2010-192369 A   9/2010
(Continued)

OTHER PUBLICATIONS

Int'l Search Report dated Jun. 27, 2017 in Int'l Application No. PCT/JP2017/014103.
(Continued)

*Primary Examiner* — Caridad Everhart
(74) *Attorney, Agent, or Firm* — Panitch Schwarze Belisario & Nadel LLP

(57) ABSTRACT

A composition is provided which contains a fluorinated alcohol represented by formula (1) and a charge transporting compound:

$$C_{nF}H_{2nF+1-mF}F_{mF}OH \quad (1)$$

nF and mF are each independently an integer of 1 or more and satisfy $2nF+1 \geq mF$. An amount of hydrogen fluoride generated from the fluorinated alcohol under atmospheric pressure at 25° C. is 5.0 ppm by volume or less.

10 Claims, 2 Drawing Sheets

(51) Int. Cl.
 *H01L 51/50* (2006.01)
 *H01L 51/56* (2006.01)
(52) U.S. Cl.
 CPC ...... *H01L 51/0003* (2013.01); *H01L 51/0072* (2013.01); *H01L 51/0074* (2013.01); *H01L 51/0085* (2013.01); *H01L 51/5056* (2013.01); *H01L 51/5072* (2013.01); *H01L 51/5088* (2013.01); *H01L 51/5092* (2013.01); *H01L 51/56* (2013.01); *H01L 2251/556* (2013.01); *H01L 2251/558* (2013.01)
(58) Field of Classification Search
 CPC ............. H01L 51/5048; H01L 51/5056; H01L 51/5072; H01L 51/5088
 See application file for complete search history.

(56) References Cited

U.S. PATENT DOCUMENTS

| | | | | |
|---|---|---|---|---|
| 2005/0227368 | A1* | 10/2005 | Ezan | G01N 33/84 436/528 |
| 2010/0267180 | A1 | 10/2010 | Kojima et al. | |
| 2013/0026475 | A1* | 1/2013 | Choi | H01L 27/1255 257/59 |
| 2014/0004656 | A1* | 1/2014 | Sasagawa | H01L 29/66969 438/104 |
| 2018/0183011 | A1* | 6/2018 | Oikawa | H01L 51/004 |

FOREIGN PATENT DOCUMENTS

| | | |
|---|---|---|
| JP | 2012-230774 A | 11/2012 |
| JP | 2013-077518 A | 4/2013 |
| JP | 2013-102101 A | 5/2013 |
| JP | 2013-166871 A | 8/2013 |
| JP | 2013-200941 A | 10/2013 |
| JP | 2014-044972 A | 3/2014 |
| WO | 2004/000987 A1 | 12/2003 |
| WO | 2009/063850 A1 | 5/2009 |
| WO | 2015/159932 A1 | 10/2015 |

OTHER PUBLICATIONS

Office Action dated Aug. 8, 2017 in JP Application No. 2017-535096.
Int'l Preliminary Report on Patentability dated Nov. 8, 2018 in Int'l Application No. PCT/JP2017/014103.

* cited by examiner

COMPOSITION

CROSS-REFERENCE TO RELATED APPLICATION

This application is a Section 371 of International Application No. PCT/JP2017/014103, filed Apr. 4, 2017, which was published in the Japanese language on Nov. 2, 2017 under International Publication No. WO 2017/187906 A1, and claims priority under 35 U.S.C. § 119(b) to Japanese Application No. 2016-087313, filed Apr. 25, 2016, the disclosures of which are incorporated herein by reference in their entirety.

TECHNICAL FIELD

The present invention relates to a composition used for an organic electroluminescent device and the like.

BACKGROUND ART

To improve properties of light emitting devices such as organic electroluminescent devices, the insertion of various layers between light emitting layers and electrodes has been examined. For example, a method for forming an electron transporting layer between a light emitting layer and an electrode using a solution obtained by dissolving an electron transporting material in fluorinated alcohol is known (Patent Literature 1).

CITATION LIST

Patent Literature

Patent Literature 1: International Publication No. WO 2009-063850

SUMMARY OF INVENTION

Technical Problem

However, the lifetime of the light emitting device obtained by the above-mentioned method is not necessarily sufficient. Then, an object of the present invention is to provide a composition useful to manufacture a long-life light emitting device.

Solution to Problem

The present invention provides the following [1] to [6].
[1] A composition comprising: a fluorinated alcohol represented by the following formula (1):

$$C_{nF}H_{2nF+1-mF}F_{mF}OH \quad (1)$$

wherein nF and mF are each independently an integer being 1 or more and satisfying $2nF+1 \geq mF$; and a charge transporting compound, wherein an amount of hydrogen fluoride generated from the fluorinated alcohol under atmospheric pressure at 25° C. is 5.0 ppm by volume or less.
[2] The composition according to [1], wherein the amount of the hydrogen fluoride is 0.01 ppm by volume or more and 5.0 ppm by volume or less.
[3] The composition according to [1] or [2], wherein the fluorinated alcohol is a primary alcohol.
[4] The composition according to any one of [1] to [3], wherein the charge transporting compound is at least one selected from the group consisting of aromatic hydrocarbon compounds; aromatic heterocyclic compounds; organosilane compounds; alkali metal salts and alkaline earth metals salts thereof, halides, oxide salts, and carbonates of alkaline metals and alkaline earth metals; and metal complexes.
[5] The composition according to any one of [1] to [4], wherein the charge transporting compound is at least one selected from the group consisting of aromatic hydrocarbon compounds and aromatic heterocyclic compounds.
[6] The composition according to any one of [1] to [4], wherein the charge transporting compound is at least one selected from the group consisting of alkali metal salts and alkaline earth metal salts of aromatic hydrocarbon compounds; and alkali metal salts and alkaline earth metal salts of aromatic heterocyclic compounds.

Advantageous Effects of Invention

According to the present invention, a composition useful to manufacture a long-life light emitting device can be provided.

DESCRIPTION OF EMBODIMENTS

Figure 1:
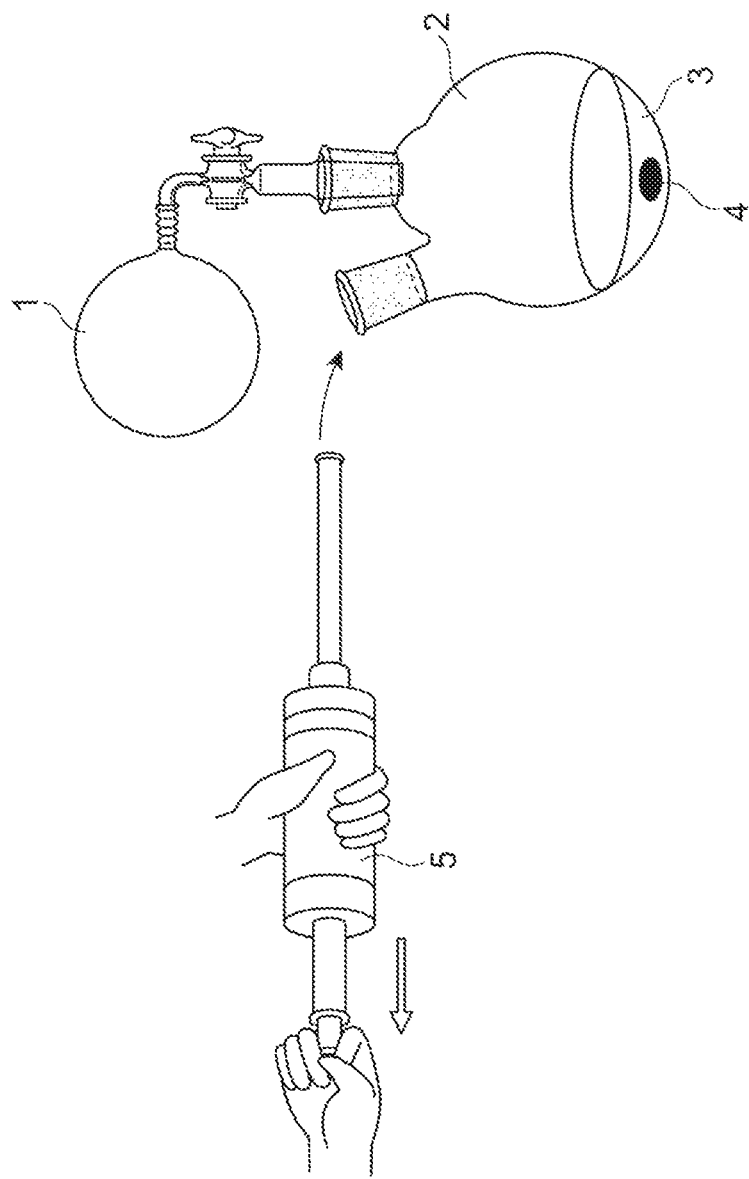
FIG. 1 is a schematic diagram showing a method for measuring the amount of hydrogen fluoride.

Preferable embodiments of the present invention will now be described in detail.

<Description of Common Terms>

Unless otherwise stated, terms commonly used in the present specification have the following meanings.

Me represents a methyl group, Et represents an ethyl group, Bu represents a butyl group, i-Pr represents an isopropyl group, and t-Bu represents a tert-butyl group.

The hydrogen atom may be a heavy hydrogen atom or a light hydrogen atom.

In the formula representing a metal complex, a solid line representing a bond to the central metal represents a covalent bond or a coordinate bond.

The term "polymer compound" means a polymer having molecular weight distribution and having a polystyrene-equivalent number-average molecular weight of $1 \times 10^3$ to $1 \times 10^8$.

The polymer compound may be any of a block copolymer, a random copolymer, an alternating copolymer, and a graft copolymer, or may even be some other form.

If a polymerization active group remains intact at the terminal group of the polymer compound, light emitting properties or luminance lifetime may deteriorate if such a polymer compound is used to fabricate the light emitting device, and therefore, it is preferable that the terminal group be a stable group. This terminal group is preferably a group covalently bonded to the main chain, and examples thereof include groups bonding to an aryl group or a monovalent heterocyclic group via a carbon-carbon bond.

The term "low molecular weight compound" means a compound that does not have a molecular weight distribution and that has a molecular weight of $1 \times 10^4$ or less.

The term "constitutional unit" means a unit occurring one or more times in a polymer compound.

The "alkyl group" may be either linear or branched. The linear alkyl group has, for example, 1 to 50 carbon atoms, preferably 3 to 30 carbon atoms, and more preferably 4 to 20 carbon atoms, not including the carbon atoms of the substituent. The branched alkyl group has, for example, 3 to 50 carbon atoms, preferably 3 to 30 carbon atoms, and more preferably 4 to 20 carbon atoms, not including the carbon atoms of the substituent.

The alkyl group may have a substituent, and examples thereof include a methyl group, an ethyl group, a propyl group, an isopropyl group, a butyl group, a 2-butyl group, an isobutyl group, a tert-butyl group, a pentyl group, an isoamyl group, 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group, and a dodecyl group, and groups obtained by substituting a hydrogen atom of these groups with a cycloalkyl group, an alkoxy group, a cycloalkoxy group, an aryl group, a fluorine atom, and the like; and examples thereof include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl)propyl group, and a 6-ethyloxyhexyl group.

The "cycloalkyl group" has, for example, 3 to 50 carbon atoms, preferably 3 to 30 carbon atoms, and more preferably 4 to 20 carbon atoms, not including the carbon atoms of the substituent.

The cycloalkyl group may have a substituent, and examples thereof include a cyclohexyl group, a cyclohexylmethyl group, and a cyclohexylethyl group.

The term "aryl group" means the atomic group remaining after removing from an aromatic hydrocarbon one hydrogen atom that is directly bonded to a carbon atom constituting the ring. The aryl group has, for example, 6 to 60 carbon atoms, preferably 6 to 20 carbon atoms, and more preferably 6 to 10 carbon atoms, not including the carbon atoms of the substituent.

The aryl group may have a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, and a 4-phenylphenyl group, and groups obtained by substituting a hydrogen atom of these groups with an alkyl group, a cycloalkyl group, an alkoxy group, a cycloalkoxy group, an aryl group, a fluorine atom, and the like.

The "alkoxy group" may be any of linear and branched. The linear alkoxy group has, for example, 1 to 40 carbon atoms, and preferably 4 to 10 carbon atoms, not including the carbon atoms of the substituent. The branched alkoxy group has, for example, 3 to 40 carbon atoms, and preferably 4 to 10 carbon atoms, not including the carbon atoms of the substituent.

The alkoxy group may have a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group, and a lauryloxy group, and groups obtained by substituting a hydrogen atom of these groups with a cycloalkyl group, an alkoxy group, a cycloalkoxy group, an aryl group, a fluorine atom, and the like.

The "cycloalkoxy group" has, for example, 3 to 40 carbon atoms, and preferably 4 to 10 carbon atoms, not including the carbon atoms of the substituent.

The cycloalkoxy group may have a substituent, and examples thereof include a cyclohexyloxy group.

The "aryloxy group" has, for example, 6 to 60 carbon atoms, and preferably 6 to 48, not including the carbon atoms of the substituent.

The aryloxy group may have a substituent, and examples thereof include a phenoxy group, a 1-naphthyloxy group, a 2-naphthyloxy group, a 1-anthracenyloxy group, a 9-anthracenyloxy group, and a 1-pyrenyloxy group, and groups obtained by substituting a hydrogen atom of these groups with an alkyl group, a cycloalkyl group, an alkoxy group, a cycloalkoxy group, a fluorine atom, and the like.

The term "p-valent heterocyclic group" (p represents an integer of 1 or more) means an atomic group remaining after removing from a heterocyclic compound p atoms of hydrogen among the hydrogen atoms that are directly bonded to carbon atoms or hetero atoms constituting the ring. Among p-valent heterocyclic groups, preferable are "p-valent aromatic heterocyclic groups", which are the atomic groups remaining after p atoms of hydrogen among the hydrogen atoms directly bonded to carbon atoms or hetero atoms constituting the ring are removed from an aromatic heterocyclic compound.

The term "aromatic heterocyclic compound" means, for example, a compound in which the heterocyclic ring itself exhibits aromaticity, such as oxadiazole, thiadiazole, thiazole, oxazole, thiophene, pyrrole, phosphole, furan, pyridine, pyrazine, pyrimidine, triazine, pyridazine, quinoline, isoquinoline, azole, diazole, triazole, carbazole, azacarbazole, diazacarbazole, dibenzophosphole, and the like, or a compound in which an aromatic ring is condensed to a heterocyclic ring even if the heterocyclic ring itself does not exhibit aromaticity, such as phenoxazine, phenothiazine, dibenzoborole, dibenzosilole, benzopyran, and the like.

The monovalent heterocyclic group has, for example, 2 to 60 carbon atoms, and preferably 4 to 20 carbon atoms, not including the carbon atoms of the substituent.

The monovalent heterocyclic group may have a substituent, and examples thereof include a thienyl group, a pyrrolyl group, a furyl group, a pyridyl group, a piperidinyl group, a quinolinyl group, an isoquinolinyl group, a pyrimidinyl group and a triazinyl group, and groups obtained by substituting a hydrogen atom of these groups with an alkyl group, a cycloalkyl group, an alkoxy group, a cycloalkoxy group, and the like.

The term "halogen atom" means a fluorine atom, a chlorine atom, a bromine atom, or an iodine atom.

An "amino group" may have a substituent, and a substituted amino group is preferable. As the substituent that the amino group has, an alkyl group, a cycloalkyl group, an aryl group, or a monovalent heterocyclic group is preferable.

Examples of the substituted amino group include a dialkylamino group, a dicycloalkylamino group, and a diarylamino group.

Examples of the amino group include a dimethylamino group, a diethylamino group, a diphenylamino group, a bis(4-methylphenyl)amino group, a bis(4-tert-butylphenyl) amino group, and a bis(3,5-di-tert-butylphenyl)amino group.

An "alkenyl group" may be any of linear and branched. The linear alkenyl group has, for example, 2 to 30 carbon atoms, and preferably 3 to 20 carbon atoms, not including the carbon atoms of the substituent. The branched alkenyl group has, for example, 3 to 30 carbon atoms, and preferably 4 to 20 carbon atoms, not including the carbon atoms of the substituent.

A "cycloalkenyl group" has, for example, 3 to 30 carbon atoms, and preferably 4 to 20 carbon atoms, not including the carbon atoms of the substituent.

The alkenyl group and the cycloalkenyl group may have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, and a 7-octenyl group, and these groups having a substituent.

An "alkynyl group" may be any of linear and branched. The alkynyl group has, for example, 2 to 20 carbon atoms, and preferably 3 to 20 carbon atoms, not including the carbon atoms of the substituent. The branched alkynyl group has, for example, 4 to 30 carbon atoms, and preferably 4 to 20 carbon atoms, not including the carbon atoms of the substituent.

A "cycloalkynyl group" has, for example, 4 to 30 carbon atoms, and preferably 4 to 20 carbon atoms, not including the carbon atoms of the substituent.

The alkynyl group and the cycloalkynyl group may have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group and a 5-hexynyl group, and these groups having a substituent.

An "arylene group" means an atomic group remaining after removing from an aromatic hydrocarbon two hydrogen atoms that are directly bonded to a carbon atom constituting the ring. The arylene group has, for example, 6 to 60 carbon atoms, preferably 6 to 30 carbon atoms, and more preferably 6 to 18 carbon atoms, not including the carbon atoms of the substituent.

The arylene group may have a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, and preferable are groups represented by formula (A-1) to formula (A-20). The arylene group may be a group obtained by bonding a plurality of these groups.

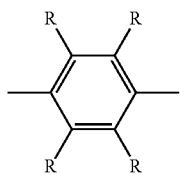
(A-1)

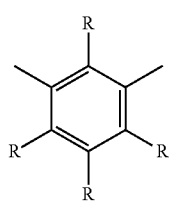
(A-2)

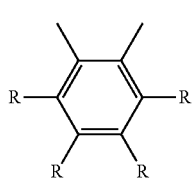
(A-3)

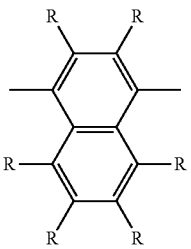
(A-4)

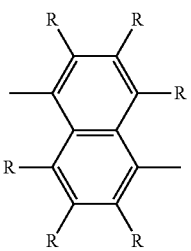
(A-5)

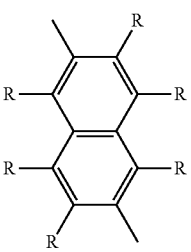
(A-6)

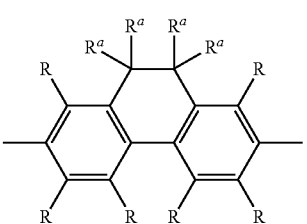
(A-7)

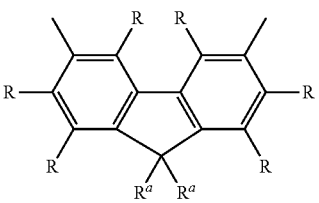
(A-8)

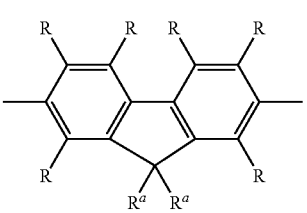
(A-9)

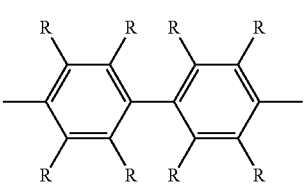
(A-10)

(A-11)
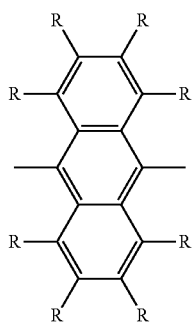
(A-12)
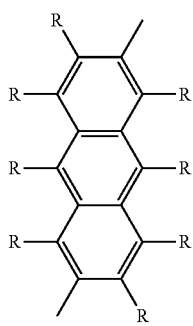
(A-13)
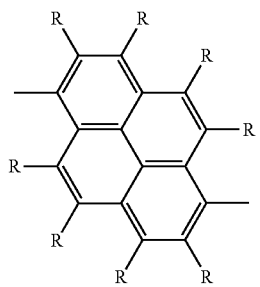
(A-14)
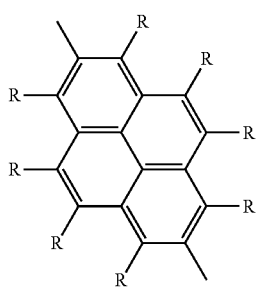
(A-15)
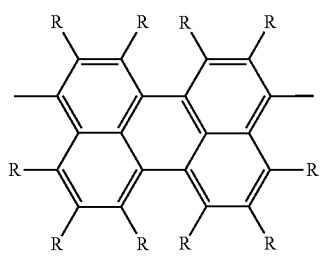
(A-16)
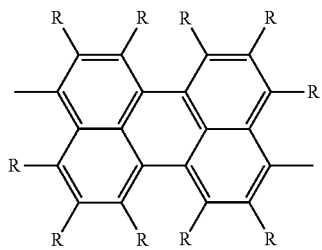
(A-17)
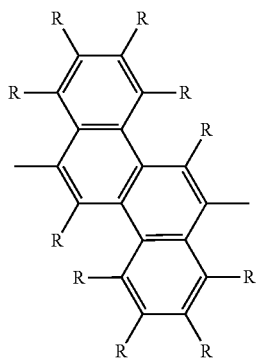
(A-18)
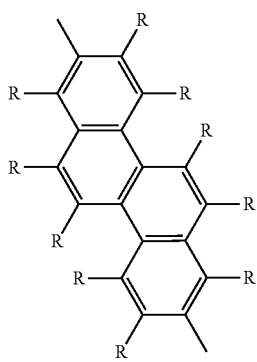
(A-19)
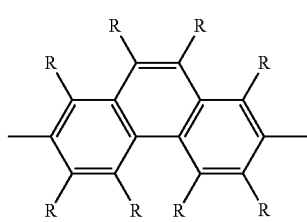
(A-20)
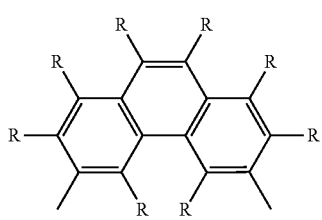
In the formulas, R and $R^a$ each independently represent a hydrogen atom, an alkyl group, a cycloalkyl group, an aryl group or a monovalent heterocyclic group; a plurality of R and $R^a$ each may be the same or different; and the plurality of R may be bonded to each other to form a ring together with the atoms to which they are bonded.

The divalent heterocyclic group has, for example, 2 to 60 carbon atoms, preferably 3 to 20 carbon atoms, and more preferably 4 to 15 carbon atoms, not including the carbon atoms of the substituent.

The divalent heterocyclic group may have a substituent, and examples thereof include divalent groups obtained by removing from pyridine, diazabenzene, triazine, azanaphthalene, diazanaphthalene, carbazole, azacarbazole, diazacarbazole, dibenzofuran, dibenzothiophene, dibenzosilole, phenoxazine, phenothiazine, acridine, dihydroacridine, furan, thiophene, azole, diazole and triazole two hydrogen atoms among the hydrogen atoms directly bonded to a carbon atom or a hetero atom constituting the ring. Preferable are groups represented by formula (AA-1) to formula (AA-38). The divalent heterocyclic group may be a group obtained by bonding a plurality of these groups.

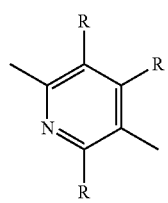

(AA-1)

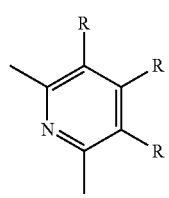

(AA-2)

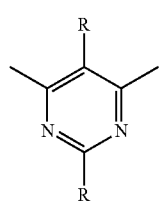

(AA-3)

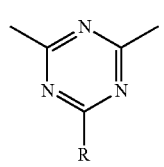

(AA-4)

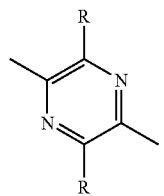

(AA-5)

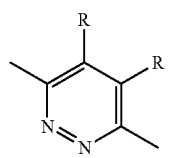

(AA-6)

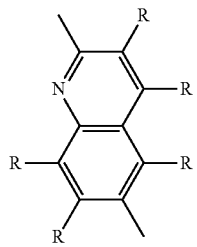

(AA-7)

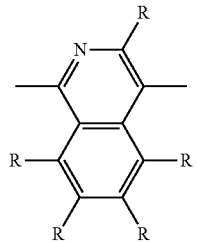

(AA-8)

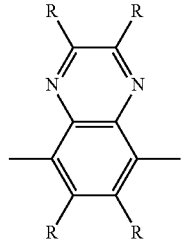

(AA-9)

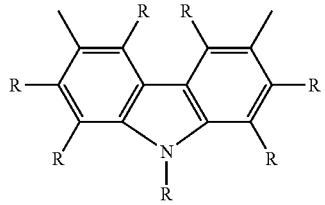

(AA-10)

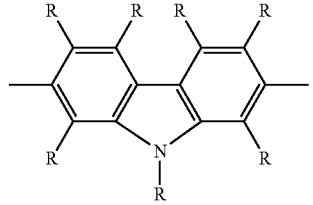

(AA-11)

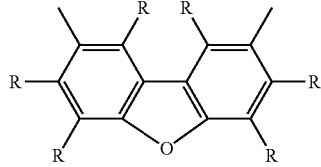

(AA-12)

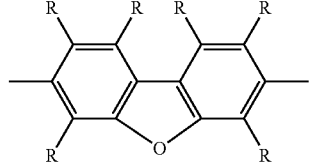

(AA-13)

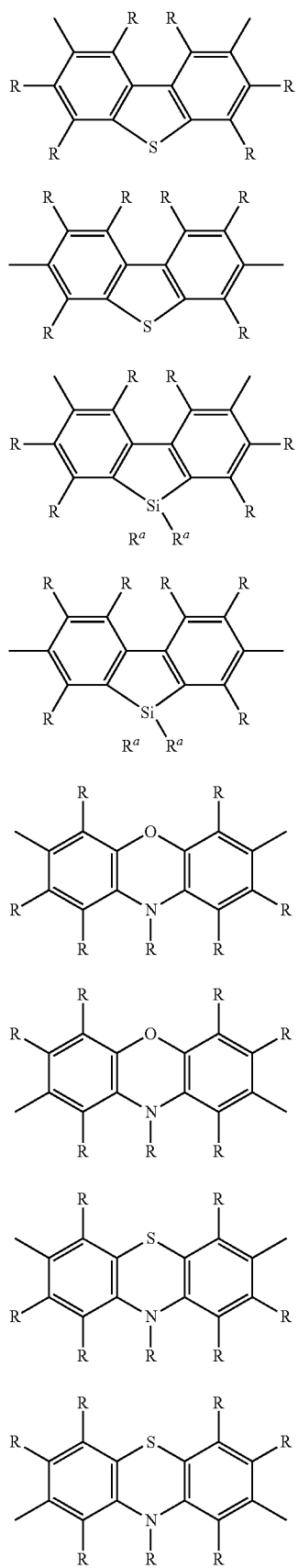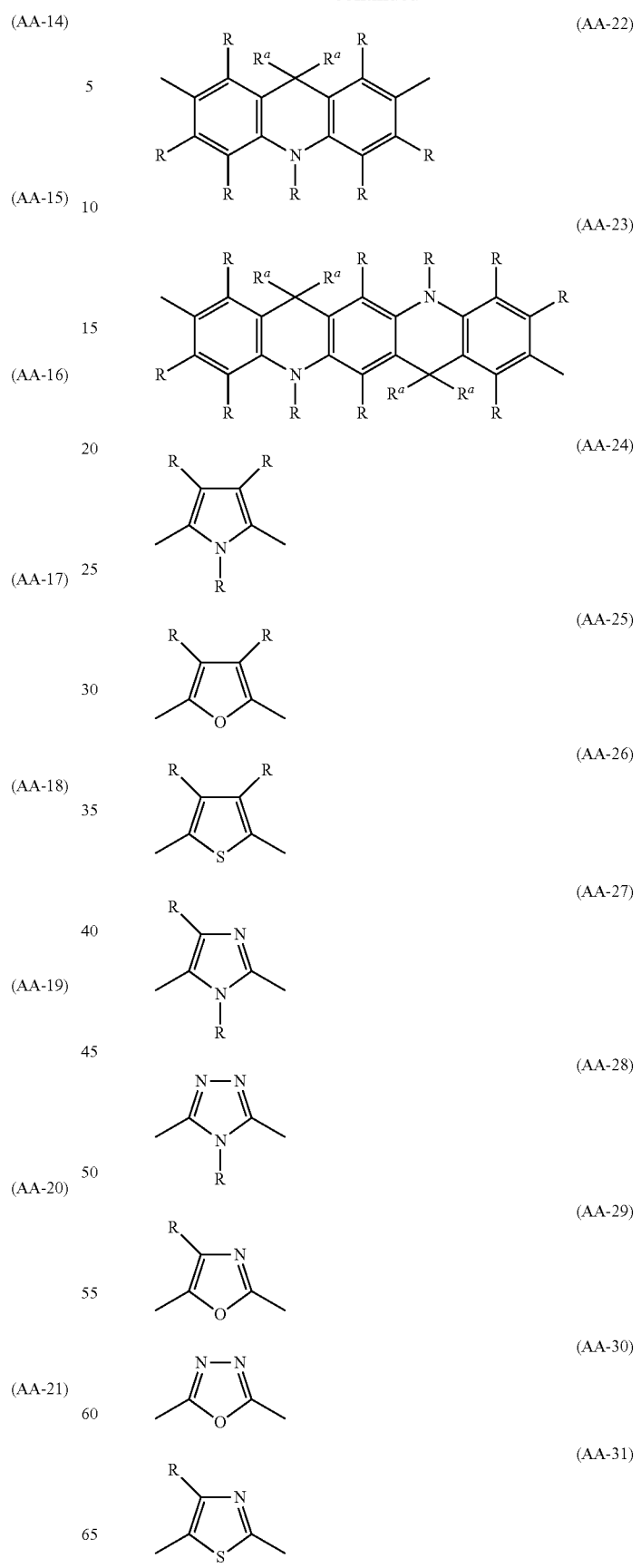

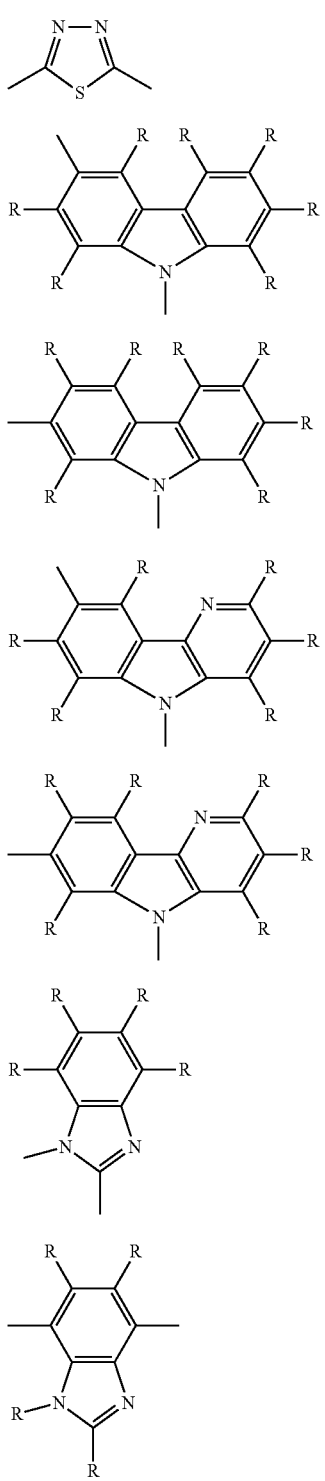
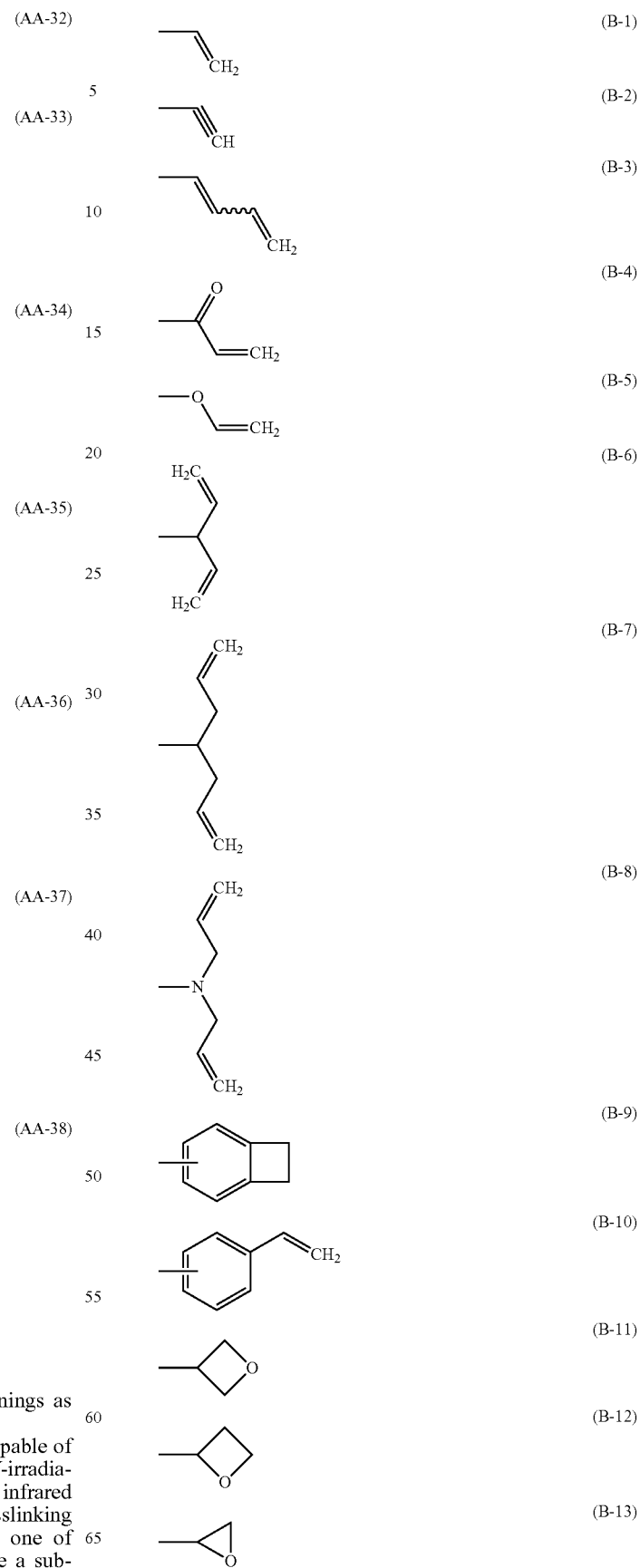

In the formulas, R and R$^a$ have the same meanings as described above.

The term "crosslinking group" means a group capable of producing a new bond when subjected to heat, UV-irradiation, near-UV irradiation, visible light irradiation, infrared irradiation, a radical reaction, and the like. The crosslinking group is preferably a group represented by any one of formulas (B-1) to (B-17). These groups may have a substituent.

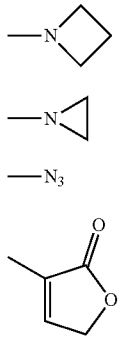

(B-14)

(B-15)

(B-16)

(B-17)

The term "substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group, or a cycloalkynyl group. The substituent may also be a crosslinking group.

The composition of the present embodiment contains a fluorinated alcohol represented by the following formula (1) and a charge transporting compound.

In the formula (1), nF and mF are each independently an integer that is 1 or more and satisfies $2nF+1 \geq mF$.

<Fluorinated Alcohol>

The fluorinated alcohol is a compound obtained by substituting one or more atoms of hydrogen other than the hydrogen atom constituting the hydroxyl group in an alcohol with fluorine atoms.

nF may be, for example, an integer of 1 to 12; is preferably an integer of 1 to 10, and more preferably an integer of 1 to 8 from the viewpoint of the viscosity of the fluorinated alcohol; and is preferably an integer of 4 to 10, and more preferably an integer of 5 to 8 from the viewpoint of the boiling point of the fluorinated alcohol.

mF may be, for example, an integer of 1 to 24, and is preferably an integer of 4 to 12, more preferably an integer of 6 to 12, and still more preferably an integer of 8 to 12 since the film formability of the composition of the present embodiment is excellent.

nF and mF satisfy $(2nF+1)-mF \geq 0$, preferably $2 \leq (2nF+1)-mF \leq 10$, more preferably $2 \leq (2nF+1)-mF \leq 6$, still more preferably $3 \leq (2nF+1)-mF \leq 6$, and particularly preferably $(2nF+1)-mF=3$.

Examples of the fluorinated alcohol represented by the formula (1) include primary alcohols, secondary alcohols and tertiary alcohols, and it is preferably a primary alcohol.

The fluorinated alcohol represented by the formula (1) may be linear or branched, and is preferably linear since the fluorinated alcohol is easily produced.

Example of the fluorinated alcohol represented by the formula (1) include 1H,1H-trifluoroethanol, 1H,1H-pentafluoropropanol, 6-(perfluoroethyl)hexanol, 1H, 1H-heptafluorobutanol, 2-(perfluorobutyl)ethanol, 3-(perfluorobutyl)propanol, 6-(perfluorobutyl)hexanol, 2-(perfluorohexyl)ethanol, 3-(perfluorohexyl)propanol, 6-(perfluorohexyl)hexanol, 6-(perfluoro-1-methylethyl)hexanol, 1H,1H,3H-tetrafluoropropanol, 1H,1H,5H-octafluoropentanol, 1H,1H,7H-dodecafluoroheptanol, 2H-hexafluoro-2-propanol and 1H,1H,3H-hexafluorobutanol, and it is preferably 1H,1H,5H-octafluoropentanol and 1H,1H,7H-dodecafluoroheptanol.

As to the above-mentioned fluorinated alcohol, the amount of hydrogen fluoride generated from the fluorinated alcohol under atmospheric pressure at 25° C. (hereinafter also simply referred to as "the amount of hydrogen fluoride") is 5.0 ppm by volume or less. Since the lifetime of the light emitting device manufactured using the composition of the present embodiment is further improved, the amount of hydrogen fluoride is preferably 0.01 ppm by volume or more and 5.0 ppm by volume or less, more preferably 0.05 ppm by volume or more and 5.0 ppm by volume or less, still more preferably 0.05 ppm by volume or more and 2.0 ppm by volume or less, and particularly preferably 0.05 ppm by volume or more and 1.0 ppm by volume or less.

As shown in FIG. 1, the amount of hydrogen fluoride is measured by the following method.

A 2 L round bottom flask 2 equipped with a balloon 1 (volume: around 1000 mL) was charged with 5 mL of a fluorinated alcohol 3, and a magnetic stirring bar 4 is placed therein. At this time, the balloon 1 is inflated to such a degree that the pressure is around atmospheric pressure in the round bottom flask 2. The fluorinated alcohol 3 is airtightly stirred at 25° C. for 1 hour. After stirring, gas in the round bottom flask 2 is injected into a hydrogen fluoride detector tube (for example, manufactured by GASTEC CORPORATION) through a Teflon (registered trademark) tube using a gas collector 5 (for example, manufactured by GASTEC CORPORATION, trade name: GV-100S), and the volume of hydrogen fluoride on the basis of the volume of the injected gas is read from the detector tube and defined as the amount of hydrogen fluoride (ppm by volume).

The composition of the present embodiment may contain a fluorinated alcohol, wherein the amount of hydrogen fluoride is 5.0 ppm by volume or less singly or in combination of two or more.

The fluorinated alcohol wherein the amount of hydrogen fluoride is 5.0 ppm by volume or less is obtained, for example, by reducing the amount of hydrogen fluoride of a fluorinated alcohol wherein the amount of hydrogen fluoride is more than 5.0 ppm by volume (for example, a fluorinated alcohol produced from tetrafluoroethylene as a starting material). Examples of the method for reducing the amount of hydrogen fluoride include a method for neutralizing a fluorinated alcohol with an alkali compound, a method for subjecting a fluorinated alcohol to liquid separation purification and a method of distilling a fluorinated alcohol, and a method for neutralizing a fluorinated alcohol with an alkali compound and a method for subjecting a fluorinated alcohol to liquid separation purification are used preferably.

Examples of the method for neutralizing a fluorinated alcohol with an alkali compound include a method for mixing a fluorinated alcohol and an alkali compound such as a metal hydroxide, a metal carbonate or an alkyl ammonium hydroxide.

In the mixture of the fluorinated alcohol and the alkali compound, the alkali compound may be all dissolved in the fluorinated alcohol, and may be suspended without dissolving the alkali compound in the fluorinated alcohol.

Examples of the metal hydroxide include hydroxides of alkaline metals and alkaline earth metals such as lithium hydroxide, sodium hydroxide, potassium hydroxide, rubidium hydroxide, cesium hydroxide, magnesium hydroxide and calcium hydroxide.

Examples of the metal carbonate include alkaline metal carbonates such as lithium carbonate, sodium carbonate, potassium carbonate and cesium carbonate.

The amount of the alkali compound used is 0.1 to 50 parts by weight on the basis of 100 part by weight of the fluorinated alcohol.

The temperature at the time of neutralization is, for example, −100 to 200° C. Neutralization time is, for example, 5 minutes or more.

The fluorinated alcohol after neutralization may be used for the composition of the present embodiment without any treatment or subjected to posttreatment after neutralization. Examples of the posttreatment include treatment of removing impurities, for example, by washing with a solvent, distillation or the like.

Examples of the method for subjecting a fluorinated alcohol to liquid separation purification include a method for subjecting a fluorinated alcohol to liquid separation purification using a solvent, a solution of a metal hydroxide, a solution of a metal carbonate, a solution of an alkylammonium hydroxide or the like.

The solvent is selected from solvents which form a separated state when mixed with a fluorinated alcohol, and examples thereof include organic solvents such as hexane, ethyl acetate, toluene, diethyl ether, tetrahydrofuran, 1,4-dioxane, dimethoxyethane, N,N-dimethylacetamide, N,N-dimethylformamide, dimethyl sulfoxide, methanol, ethanol, propanol, and ethylene glycol; and water. These solvents may be used singly or in combination of two or more.

When a solution of a hydroxide, a metal carbonate or an alkylammonium hydroxide in a solvent or the like is used, the concentration of the solution is, for example, 0.1 to 50% by weight.

The fluorinated alcohol after liquid separation may be used for the composition of the present embodiment without any treatment, and may be further subjected to posttreatment after liquid separation. Examples of the posttreatment include treatment of removing impurities, for example, by drying over a drying agent, distillation or the like.

<Charge Transporting Compound>

Examples of the charge transporting compound include hole transporting compounds, hole injecting compounds, electron transporting compounds and electron injecting compounds.

As the hole transporting compound and the hole injecting compound, known hole transporting compounds and hole injecting compounds can be used, and examples thereof include carbazole and derivatives thereof, triazole and derivatives thereof, oxazole and derivatives thereof, oxadiazole and derivatives thereof, imidazole and derivatives thereof, fluorene and derivatives thereof, polyarylalkanes and derivatives thereof, pyrazoline and derivatives thereof, pyrazolone and derivatives thereof, phenylenediamine and derivatives thereof, arylamines and derivatives thereof, starburst amines, phthalocyanine and derivatives thereof, amino-substituted calcone and derivatives thereof, styryl anthracene and derivatives thereof, fluorenone and derivatives thereof, hydrazone and derivatives thereof, stilbene and derivatives thereof, silazanes and derivatives thereof, aromatic tertiary amine compounds, styryl amine compounds, aromatic dimethylidene compounds, porphyrin compounds, polysilane compounds, polyvinyl carbazole (poly(N-vinyl carbazole)) and derivatives thereof, polyarylenes having aromatic amine structures in the main chain or side chains and derivatives thereof, organosilane compounds, and polymers containing these; conductive metal oxides such as vanadium oxide, tantalum oxide, tungsten oxide, molybdenum oxide, ruthenium oxide and aluminum oxide; conductive polymers and oligomers such as polyaniline, aniline copolymers, thiophene oligomers, and polythiophene; organic conductive materials such as poly(3,4-ethylene dioxythiophene)-polystyrene sulfonate and polypyrrole, and polymers containing these; amorphous carbon; acceptor organic compounds such as tetracyanoquinodimethane and derivatives thereof (for example, 2,3,5,6-tetrafluoro-7,7,8,8-tetracyanoquinodimethane), 1,4-naphthoquinone and derivatives thereof, diphenoquinone and derivatives thereof, and polynitro compounds; silane coupling agents such as octadecyltrimethoxysilane, and aromatic amine polymer compounds.

As the electron transporting compound and the electron injecting compound, known electron transporting compounds and electron injecting compounds can be used, and example thereof include triazole and derivatives thereof, oxazole and derivatives thereof, oxadiazole and derivatives thereof, imidazole and derivatives thereof, fluorene and derivatives thereof, benzoquinone and derivatives thereof, naphthoquinone and derivatives thereof, anthraquinone and derivatives thereof, tetracyanoanthraquinodimethane and derivatives thereof, fluorenone and derivatives thereof, diphenyldicyanoethylene and derivatives thereof, diphenoquinone and derivatives thereof, anthraquinodimethane and derivatives thereof, anthrone and derivatives thereof, thiopyran dioxide and derivatives thereof, carbodiimides and derivatives thereof, fluorenylidenemethane and derivatives thereof, distyrylpyrazine and derivatives thereof, aromatic hydrocarbon compounds and aromatic heterocyclic compounds represented by tetracarboxylic acid anhydrides having aromatic rings such as naphthalene and perylene; phthalocyanine and derivatives thereof; metal complexes of 8-quinolinol and derivatives thereof and metal phthalocyanines; various metal complexes represented by metal complexes having benzoxazole and benzothiazole as ligands; organosilane compounds; and metal complexes of 8-hydroxyquinoline and derivatives thereof. The electron transporting compound and the electron injecting compound may be alkali metal salts and alkaline earth metal salts of the above-mentioned compounds as well as salts such as halides, oxide salts and carbonates of alkaline metals and alkaline earth metals.

The electron transporting compound and the electron injecting compound are preferably aromatic hydrocarbon compounds or aromatic heterocyclic compounds; or alkali metal salts or alkaline earth metal salts of these. Since the electron transporting compound and the electron injecting compound remarkably increase the lifetime of the light emitting device by adjusting the amount of hydrogen fluoride in a predetermined range, they are particularly preferably salts constituted by carboxylate ions and alkali metal ions or alkaline earth metal ions among such salts.

The electron transporting compound and the electron injecting compound may each be used singly or in combination of two or more.

The electron transporting compound and the electron injecting compound may be polymer compounds, or low molecular weight compounds.

When the electron transporting compound and the electron injecting compound are polymer compounds, as the polymer compounds, polymer compounds comprising at least one constitutional unit selected from the group consisting of constitutional units represented by formula (ET-1) are preferable.

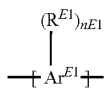 (ET-1)

In the formula, nE1 represents an integer of 0 or more, $Ar^{E1}$ represents an aromatic hydrocarbon group or a heterocyclic group, and these groups may have a substituent other than $R^{E1}$, and $R^{E1}$ represents a group represented by formula (ES-1); when there are a plurality of $R^{E1}$, they may be the same or different.

Herein, the term "aromatic hydrocarbon group" means an atomic group remaining after removing hydrogen atoms directly bonded to carbon atoms constituting the ring from an aromatic hydrocarbon.

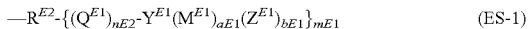 (ES-1)

In the formula, nE2 represents an integer of 0 or more, aE1 represents an integer of 1 or more, bE1 represents an integer of 0 or more, and mE1 represents an integer of 1 or more; when there are a plurality of nE2, aE1, and bE1, they may be the same or different; however, when $R^{E3}$ is a single bond, mE1 is 1; and aE1 and bE1 are selected so that the charge of the group represented by formula (ES-1) is zero, $R^{E2}$ represents a single bond, a hydrocarbon group, a heterocyclic group or —O—$R^{E2'}$ ($R^{E2'}$ represents a hydrocarbon group or a heterocyclic group), and these groups may have a substituent, $Q^{E1}$ represents an alkylene group, a cycloalkylene group, an arylene group, an oxygen atom, or a sulfur atom, and these groups may have a substituent; and when there are a plurality of $Q^{E1}$, they may be the same or different, $Y^{E1}$ represents $CO_2^-$, $SO_3^-$, $SO_2^-$, or $PO_3^{2-}$; and when there are a plurality of $Y^{E1}$, they may be the same or different, $M^{E1}$ represents an alkali metal cation, an alkali earth metal cation, or an ammonium cation, and the ammonium cation may have a substituent; when there are a plurality of $M^{E1}$, they may be the same or different, and $Z^{E1}$ represents $F^-$, $Cl^-$, $Br^-$, $FI^-$, $OH^-$, $B(R^{E4})_4^-$, $R_{E4}SO_3^-$, $R^{E4}COO^-$, $NO_3^-$, $SO_4^{2-}$, $HSO_4^-$, $PO_4^{3-}$, $HPO_4^{2-}$, $H_2PO_4^-$, $BF_4^-$, or $PF_6^-$; $R^{E4}$ represents an alkyl group, a cycloalkyl group, or an aryl group, and these groups may have a substituent; and when there are a plurality of $Z^{E1}$, they may be the same or different.

Herein, the term "hydrocarbon group" means an atomic group remaining after removing hydrogen atoms directly bonded to carbon atoms from an aliphatic hydrocarbon and an atomic group remaining after removing hydrogen atoms directly bonded to carbon atoms constituting the ring from an aromatic hydrocarbon.

nE1 is, for example, an integer of 0 to 4, and preferably 1 or 2.

As the aromatic hydrocarbon group or the heterocyclic group represented by $Ar^{E1}$, groups obtained by removing nE1 atoms of hydrogen directly bonded to atoms constituting the ring from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, a 2,7-phenanthrenediyl group or a 2,7-carbazolediyl group are preferable, groups obtained by removing nE1 atoms of hydrogen directly bonded to atoms constituting the ring from a 2,7-fluorenediyl group or a 3,6-fluorenediyl group may be more preferable, and they may have a substituent other than $R^{E1}$.

Examples of the optional substituent other than $R^{E1}$ of $Ar^{E1}$ include a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group, a cycloalkynyl group, a carboxyl group, and a group represented by formula (ES-3), and an alkyl group is preferable.

 (ES-3)

In the formula, n', m', and nx each independently represent an integer of 1 or more.

n' is, for example, an integer of 1 to 10, preferably an integer of 1 to 6, and more preferably 2 or 3.

m' is, for example, an integer of 1 to 10, preferably an integer of 1 to 6, and more preferably 1 or 2.

nx is, for example, an integer of 1 to 10, preferably an integer of 1 to 6, and more preferably an integer of 2 to 4.

nE2 is, for example, an integer of 0 to 10, preferably an integer of 0 to 8, and more preferably an integer of 0 to 2.

aE1 is, for example, an integer of 1 to 10, preferably an integer of 1 to 5, and more preferably 1 or 2.

bE1 is, for example, an integer of 0 to 10, preferably an integer of 0 to 4, and more preferably 0 or 1.

mE1 is, for example, an integer of 1 to 5, preferably 1 or 2, and more preferably 1.

When $R^{E2}$ is —O—$R^{E2'}$, the group represented by formula (ES-1) is a group represented by the following formula.

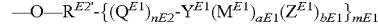

$R^{E2}$ is preferably a hydrocarbon group or a heterocyclic group, more preferably an aromatic hydrocarbon group or an aromatic heterocyclic group, and still more preferably an aromatic hydrocarbon group.

Examples of the optional substituent of $R^{E2}$ include an alkyl group, a cycloalkyl group, an aryl group, a monovalent heterocyclic group, and a group represented by formula (ES-3), and a group represented by formula (ES-3) is preferable.

$Q^{E1}$ is preferably an alkylene group, an arylene group, or an oxygen atom, and more preferably an alkylene group or an oxygen atom.

$y^{E1}$ is preferably $CO_2^-$, $SO_3^-$, or $PO_3^{2-}$, and more preferably $CO_2^-$.

Examples of the alkali metal cation represented by $M^{E1}$ include $Li^+$, $Na^+$, $K^+$, $Rb^+$, and $Cs^+$, and $K^+$, $Rb^+$, or $Cs^+$ is preferable and $Cs^+$ is more preferable.

Examples of the alkali earth metal cation represented by $M^{E1}$ include $Be^{2+}$, $Mg^{2+}$, $Ca^{2+}$, $Sr^{2+}$, $Ba^{2+}$, and $Mg^{2+}$, $Ca^{2+}$, $Sr^{2+}$, and $Ba^{2+}$ are preferable, and $Ba^{2+}$ is more preferable.

Preferable examples of $M^{E1}$ include an alkali metal cation or an alkali earth metal cation, and an alkali metal cation is more preferable.

$Z^{E1}$ is preferably $F^-$, $Cl^-$, $Br^-$, $I^-$, $OH^-$, $B(R^{E4})_4^-$, $R^{E4}SO_3^-$, $R^{E4}COO^-$, or $NO_3^-$, and more preferably $F^-$, $Cl^-$, $Br^-$, $I^-$, $OH^-$, $R^{E4}SO_3^-$, or $R^{E4}COO^-$. $R_{E4}$ is preferably an alkyl group.

Examples of the group represented by formula (ES-1) include groups represented by the following formulas.

-continued

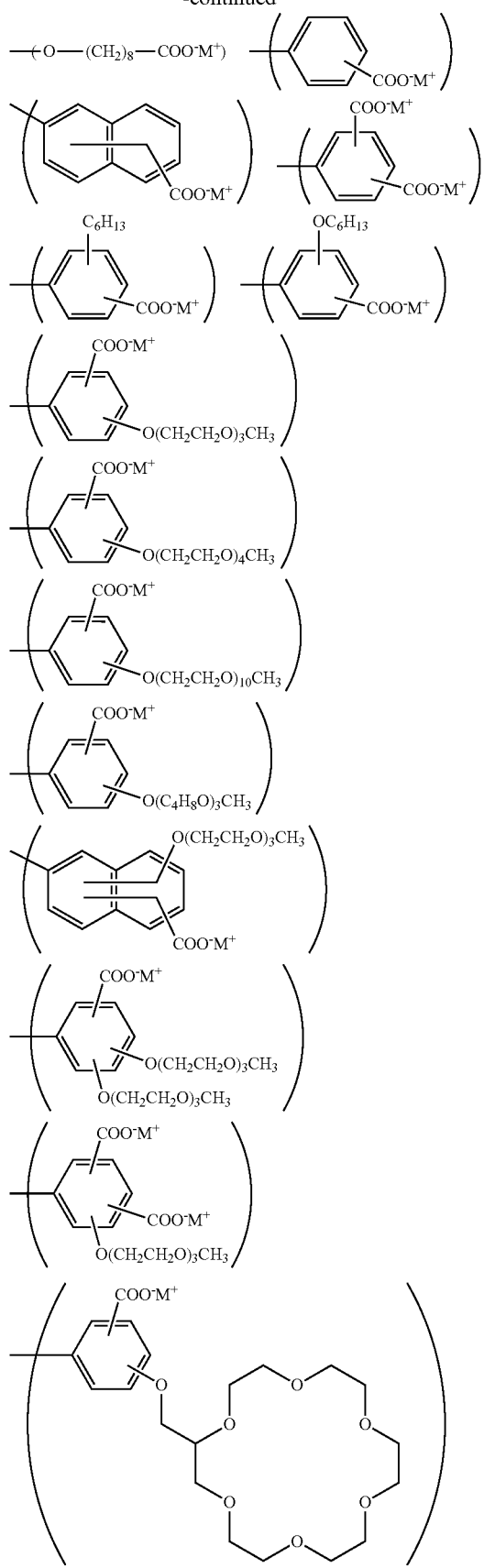

In the formulas, M⁺ represents $Li^+$, $Na^+$, $K^+$, $Cs^+$, or $N(CH^3)_4{}^+$; and when there are a plurality of $M^+$, they may be the same or different.

Examples of the constitutional unit represented by formula (ET-1) include constitutional units represented by the following formula (ET-31) to formula (ET-38), and the constitutional unit represented by formula (ET-31) or formula (ET-33) is preferable.

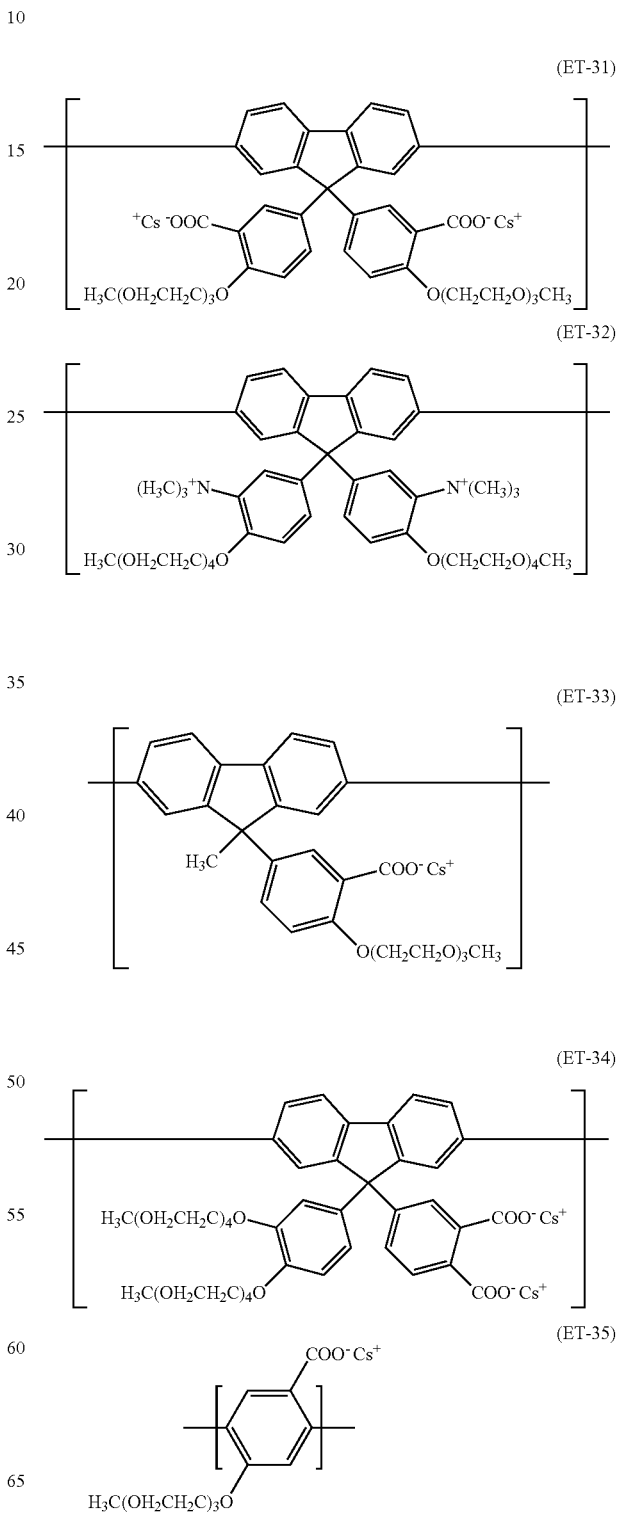

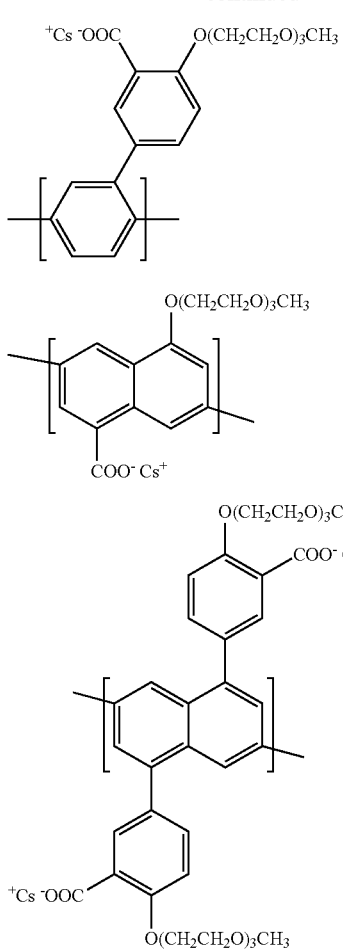

(ET-36)

(ET-37)

(ET-38)

When the electron transporting compound and the electron injecting compound are polymer compounds, the polymer compound can be synthesized according to the methods described in, for example, Japanese Unexamined Patent Publication No. 2009-239279, Japanese Unexamined Patent Publication No. 2012-033845, Japanese Unexamined Patent Publication No. 2012-216821, Japanese Unexamined Patent Publication No. 2012-216822, and Japanese Unexamined Patent Publication No. 2012-216815.

When the electron transporting compound and the electron injecting compound are low molecular weight compounds, as the low molecular weight compounds, the compound represented by formula (H-1) is preferable.

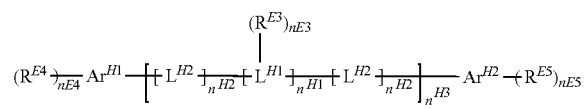

(H-1)

In the formula, $L^{H1}$ represents a group obtained by removing nE3 atoms of hydrogen from an arylene group or a divalent heterocyclic group, a group represented by $-[C(R^{H11})_2]n^{H11}-$, or a group represented by $-[P(=O)(R^{H12})]_n^{H12}-$, and these groups may have a substituent other than $R^{E3}$; when there are a plurality of $L^{H1}$, they may be the same or different;

$n^{H11}$ and $n^{H12}$ each independently represent an integer of 1 or more and 10 or less; $R^{H11}$ and $R^{H12}$ each independently represent a hydrogen atom, an alkyl group, a cycloalkyl group, an alkoxy group, a cycloalkoxy group, an aryl group or a monovalent heterocyclic group, and these groups may have a substituent; a plurality of $R^{H11}$ may be the same or different and may be bonded to each other to form a ring together with the carbon atom to which they are bonded; a plurality of $R^{H12}$ may be the same or different and may be bonded to each other to form a ring together with carbon atoms to which they are bonded;

$R^{E3}$ represents a group represented by the above-mentioned formula (ES-1); when there are a plurality of $R^{E3}$, they may be the same or different;

nE3 represents an integer of 0 or more; however, when $L^{H1}$ is a group represented by $-[C(R^{H11})_2]n^{H11}-$ or a group represented by $-[P(=OX)(R^{H12})]n^{H12}-$, nE3 represents 0; when there are a plurality of nE3, they may be the same or different;

$n^{H1}$ represents 0 or 1; when there are a plurality of $n^{H1}$, they may be the same or different;

$L^{H2}$ represents a group represented by $-N(-L^{H21}-R^{H21})-$; when there are a plurality of $L^{H2}$, they may be the same or different;

$L^{H21}$ represents a single bond, an arylene group or a divalent heterocyclic group, and these groups may have a substituent; $R^{H21}$ represents a hydrogen atom, an alkyl group, a cycloalkyl group, an aryl group or a monovalent heterocyclic group, and these groups may have a substituent;

$n^{H2}$ represents 0 or 1; when there are a plurality of $n^{H2}$, they may be the same or different;

$Ar^{H1}$ represents a group obtained by removing nE4 atoms of hydrogen from an aryl group or a monovalent heterocyclic group, and these groups may have a substituent other than $R^{E4}$;

$Ar^{H2}$ represents a group obtained by removing nE5 atoms of hydrogen from an aryl group or a monovalent heterocyclic group, and these groups may have a substituent other than $R^{E4}$;

$n^{H2}$ represents 0 or 1; when there are a plurality of $n^{H2}$, they may be the same or different;

$R^{E4}$ and $R^{E5}$ each independently represent a group represented by the above-mentioned formula (ES-1); a plurality of $R^{E4}$ may be the same or different; a plurality of $R^{E5}$ may be the same or different;

nE4 and nE5 each independently represents an integer of 0 or more; when there are a plurality of nE4, they may be the same or different; when there are a plurality of nE5, they may be the same or different; and $n^{H3}$ represents an integer of 0 or more.

$n^{H1}$ is preferably 1. $n^{H2}$ is preferably 0.

$n^{H3}$ is, for example, an integer of 0 to 10, preferably an integer of 0 to 5, still more preferably an integer of 1 to 3, and particularly preferably 1.

$n^{H11}$ is preferably an integer of 1 or more and 5 or less, more preferably an integer of 1 or more and 3 or less, and still more preferably 1.

It is preferable from the viewpoint of the charge transportability of the low molecular weight compound that $L^{H1}$ be a group obtained by removing nE3 atoms of hydrogen from an arylene group or a divalent heterocyclic group, and it is preferable from the viewpoint of solubility in a fluorinated alcohol that it be a group represented by $-[P(=O)(R^{H12})]n^{H12}-$.

When $L^{H1}$ is a group obtained by removing nE3 atoms of hydrogen from the arylene group or the divalent heterocyclic group, $L^{H1}$ is a compound represented by formula (A-1) to formula (A-3), formula (A-8) to formula (A-10), formula (AA-1) to formula (AA-6), formula (AA-10) to formula (AA-21), or formula (AA-24) to formula (AA-38), more preferably a group represented by formula (A-1), formula (A-2), formula (A-8), formula (AA-2), formula (AA-4), formula (AA-10), formula (AA-12), or formula (AA-14), still more preferably a group represented by formula (A-1), formula (A-2), formula (AA-2), formula (AA-4), or formula (AA-14).

The optional substituent of $L^{H1}$ is preferably a halogen atom, an alkyl group, a cycloalkyl group, an alkoxy group, a cycloalkoxy group, an aryl group, or a monovalent heterocyclic group, more preferably an alkyl group, an alkoxy group, an aryl group, or a monovalent heterocyclic group, and still more preferably an alkyl group, an aryl group, or a monovalent heterocyclic group, and these groups may further have a substituent.

$L^{H21}$ is preferably a single bond or an arylene group; and more preferably a single bond, and the arylene group may have a substituent.

Definition and examples of the arylene group or the divalent heterocyclic group represented by $L^{H21}$ are the same as the definition and the examples of an arylene group or a divalent heterocyclic group in a group obtained by removing nE3 atoms of hydrogen from the arylene group or the divalent heterocyclic group represented by $L^{H1}$.

It is preferable that $R^{H21}$ be an aryl group or a monovalent heterocyclic group, and these groups may have a substituent.

It is preferable that the aryl group and the monovalent heterocyclic group represented by $R^{H21}$ be a phenyl group, a spirobifluorenyl group, a pyridyl group, a pyrimidinyl group, a triazinyl group, a dibenzothienyl group, a dibenzofuryl group, a carbazolyl group or an azacarbazolyl group, and it is more preferable that they be a phenyl group, a pyridyl group, a carbazolyl group or an azacarbazolyl group.

As the substituent which $R^{H21}$ may have, an alkyl group, a cycloalkoxy group, an alkoxy group, or a cycloalkoxy group may be preferable, an alkyl group or a cycloalkoxy group may be more preferable, and these groups may further have a substituent.

Definition and examples of a group obtained by removing nE4 atoms of hydrogen from the aryl group or the monovalent heterocyclic group represented by $Ar^{H1}$ and a group obtained by removing nE5 atoms of hydrogen from the aryl group or the monovalent heterocyclic group represented by Arm are the same as the definition and the examples of an aryl group and a monovalent heterocyclic group represented by $R^{H21}$.

Definition and examples of a substituent which $Ar^{H1}$ and $Ar^{H2}$ may have are the same as the definition and the examples of the substituent which $R^{H21}$ may have.

It is preferable that the compound represented by formula (H-1) be the compound represented by formula (H-2):

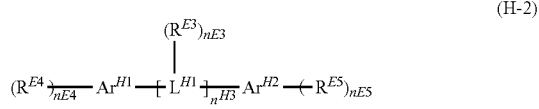

(H-2)

wherein $Ar^{H1}$, $Ar^{H2}$, $n^{H3}$, $L^{H1}$, $R^{E3}$, $R^{E4}$, $R^{E5}$, nE3, nE4 and nE5 represent the same meaning as the above.

It is preferable that at least one of nE3, nE4 and the nE5 be an integer of 1 or more.

Examples of the compound represented by formula (H-1) include the compounds represented by the following formula (H-101) to formula (H-124).

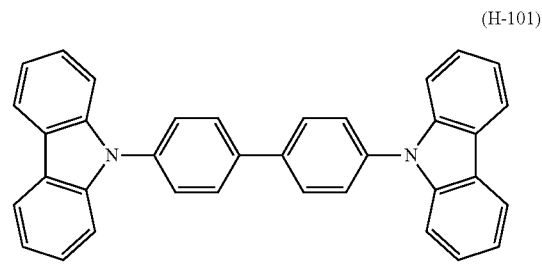

(H-101)

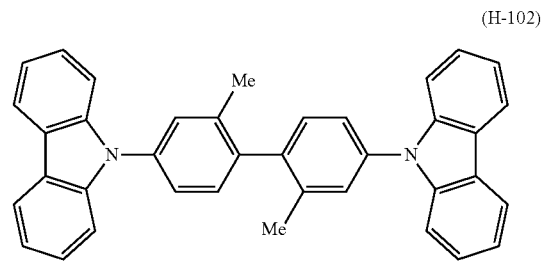

(H-102)

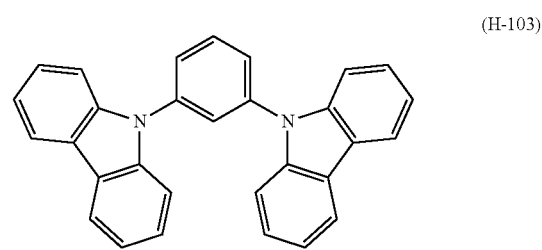

(H-103)

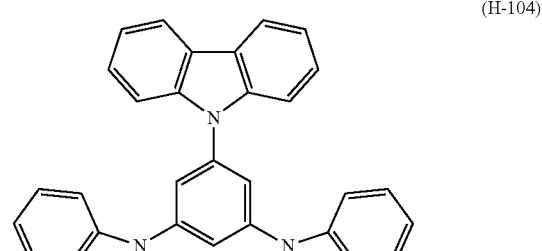

(H-104)

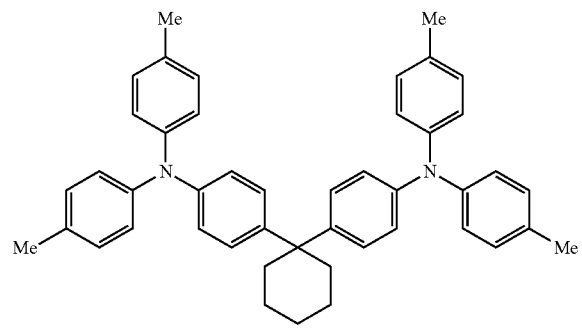

(H-105)

(H-106)
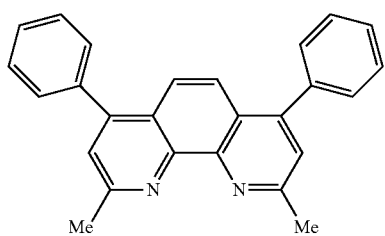
(H-107)
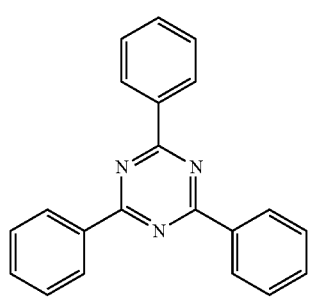
(H-108)
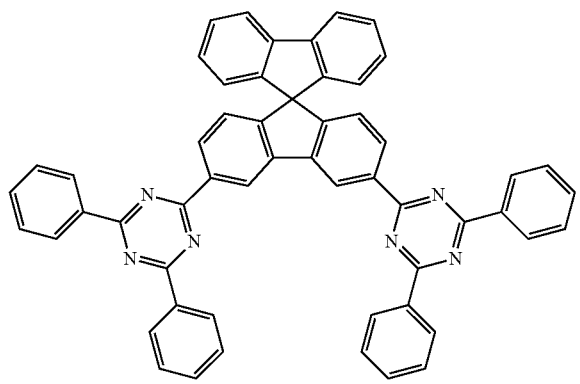
(H-109)
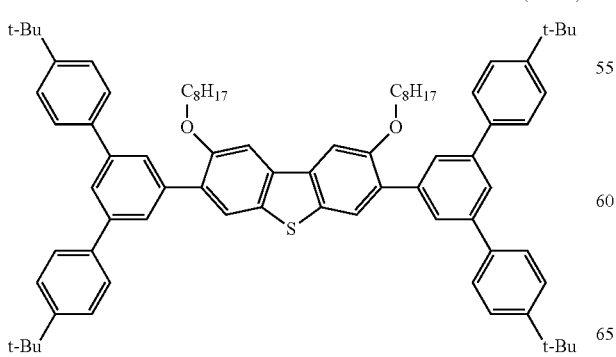
(H-110)
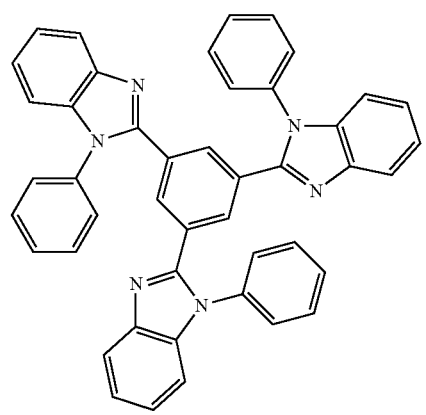
(H-111)
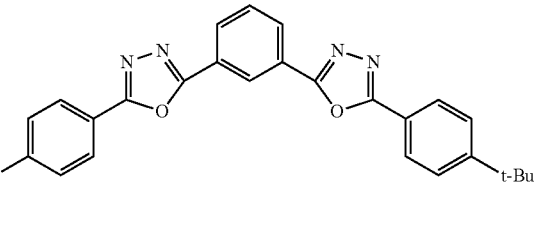
(H-112)
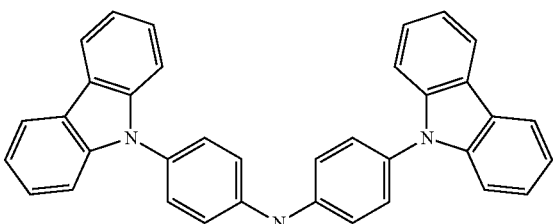
(H-113)
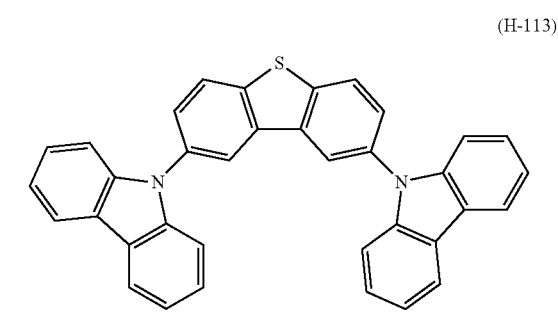

(H-114)
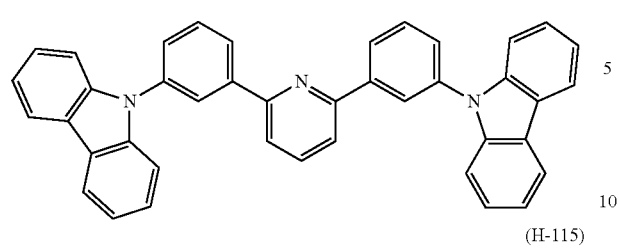
(H-115)
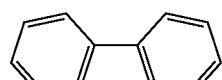
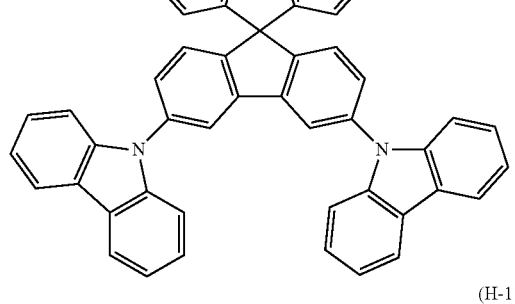
(H-116)
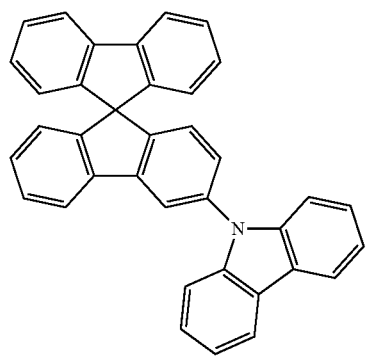
(H-117)
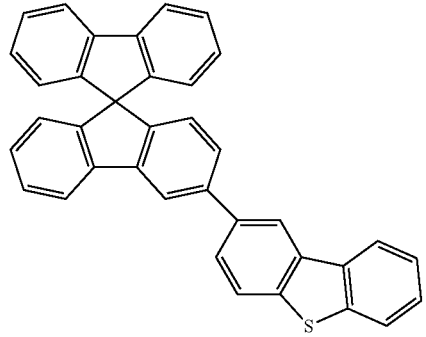
(H-118)
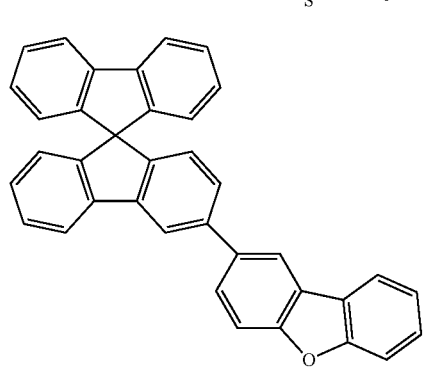
(H-119)
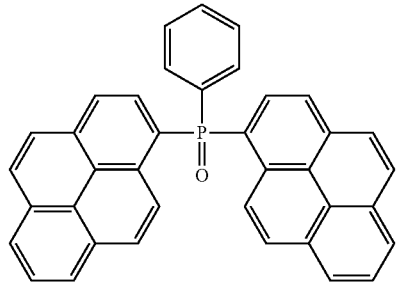
(H-120)
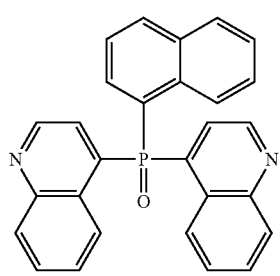
(H-121)
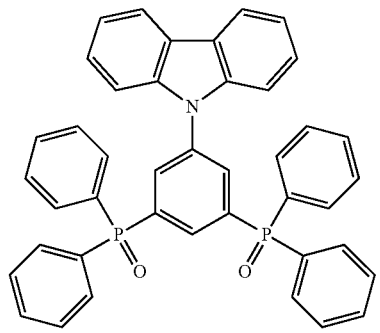
(H-122)
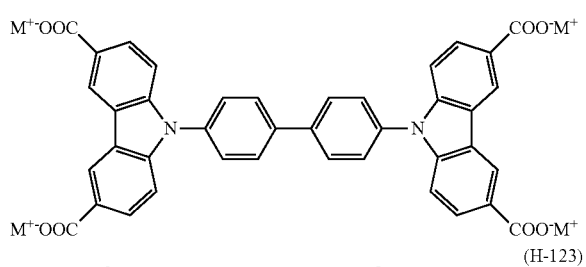
(H-123)
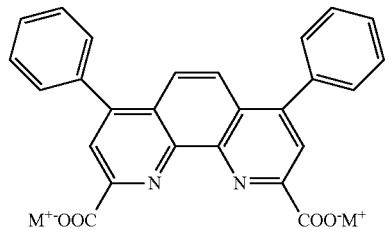

(H-124)

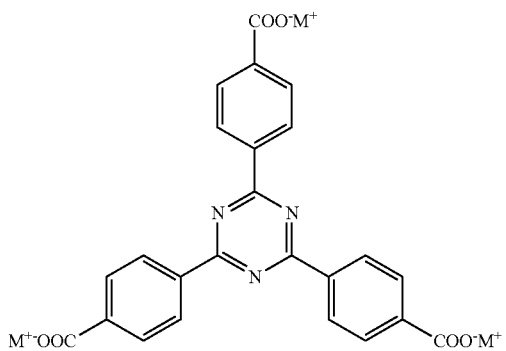

In the formulas, M⁺ represents Li⁺, Na⁺, K⁺, Cs⁺ or N(CH$_3$)$_4^+$; and when there are a plurality of M⁺, they may be the same or different.

<Light Emitting Device>

In the light emitting device containing the composition of the present embodiment, layers formed using the composition of the present embodiment are preferably one or more layers selected from the group consisting of a hole injecting layer, a hole transporting layer, an electron injecting layer, and an electron transporting layer.

The light emitting device may further comprise a layer such as a light emitting layer, a protective layer, a buffer layer, a reflective layer or a sealing layers (a sealing film, a sealing substrate or the like) which has another function.

In the light emitting device of the present embodiment, examples of a method for forming layers such as a light emitting layer, a hole transporting layer, an electron transporting layer, a hole injecting layer and an electron injecting layer include vacuum deposition from powder and a method by forming a film from a solution or a melt when a low molecular weight compound is used; and a method by forming a film from a solution or a melt when a polymer compound is used. Among these, the method by forming a film from a solution is preferable as the method for forming layers.

The order, the number and the thickness of layers to laminate may be adjusted in light of luminous efficiency and a device lifetime.

Examples of the method by forming a film from a solution include applying methods such as spin coating, casting, micro gravure printing, gravure printing, bar coating, roll coating, wire bar coating, dip coating, slit coating, cap coating, spray coating, screen printing, flexographic printing, offset printing, inkjet printing and nozzle coating.

The light emitting device may further comprise an insulating layer adjacently to an electrode to improve adhesion to the electrode and charge injection from the electrode, and may further comprise thin buffer layers on the interfaces of the hole transporting layer, the electron transporting layer or the light emitting layer for improving adhesion between interfaces, preventing the mixing thereof and the like.

[Substrate]

As long as the substrate which a light emitting device can have does not change chemically when electrodes and organic layers are formed, it may be any material, and may be substrates such as glass, plastic, a polymer film, a metal film and silicon, and a substrate obtained by layering these.

[Hole Injecting Layer]

The hole injecting layer may be formed, for example, using one or two or more of the above-mentioned hole transporting compounds (hole injecting compounds), may be formed preferably using the composition of the present embodiment containing one or two or more of the above-mentioned hole injecting compounds, and may be formed more preferably using a solution obtained by dissolving one or two or more of the above-mentioned hole injecting compounds in a solvent other than fluorinated alcohol. The thickness of the hole injecting layer is, for example, 1 nm to 1 μm.

[Hole Transporting Layer]

The hole transporting layer may be formed, for example, using one or two or more of the above-mentioned hole transporting compounds (hole injecting compounds), may be formed preferably using the composition of the present embodiment containing one or two or more of the above-mentioned hole transporting compounds, and may be formed more preferably using a solution obtained by dissolving one or two or more of the above-mentioned hole transporting compounds in a solvent other than fluorinated alcohol. The thickness of the hole transporting layer is, for example, 1 nm to 1 μm.

[Light Emitting Layer]

The light emitting layer is formed of a light emitting material. The light emitting material is classified into the low molecular weight compound and the polymer compound.

Examples of the low molecular weight compound include naphthalene and derivatives thereof, anthracene and derivatives thereof; and perylene and derivatives thereof as well as triplet emission complexes such as metal complexes having iridium, platinum or europium as a central metal and having phenylpyridine, phenylimidazole, phenyltriazole, phenylquinoline, phenanthroline, acetyl acetone or porphyrin as a ligand. These low molecular weight compounds may have crosslinking groups.

Examples of the polymer compound include a polymer compound comprising a phenylene group, a naphthalenediyl group, a fluorenediyl group, a phenanthrenediyl group, a dihydrophenanthrenediyl group, a carbazolediyl group, a phenoxazinediyl group, a phenothiazinediyl group, an anthracenediyl group, a pyrenediyl group, or the like; and polyarylenes and derivatives thereof which have an aromatic amine structure in a side chain or the main chain. These polymer compounds may have crosslinking groups.

The light emitting material preferably contains a triplet emission complex and a polymer compound.

The light emitting material may be used singly or in combination of two or more.

The light emitting layer may contain a host material with the light emitting material. The host material is classified into the low molecular weight compound and the polymer compound.

Examples of the low molecular weight compound used for a host material include the low molecular weight compounds illustrated as the hole transportation material, the low molecular weight compound illustrated as the electron transporting material, and the like, and a compound having a carbazole structure, a compound having a triarylamine structure, a compound having a phenanthroline structure, a compound having a triaryltriazine structure, a compound having an azole structure, a compound having a benzothiophene structure, a compound having a benzofuran structure, a compound having a fluorene structure, and a compound having a spirofluorene structure are preferable.

Examples of the low molecular weight compound used for a host material include compounds represented by the following formulas.

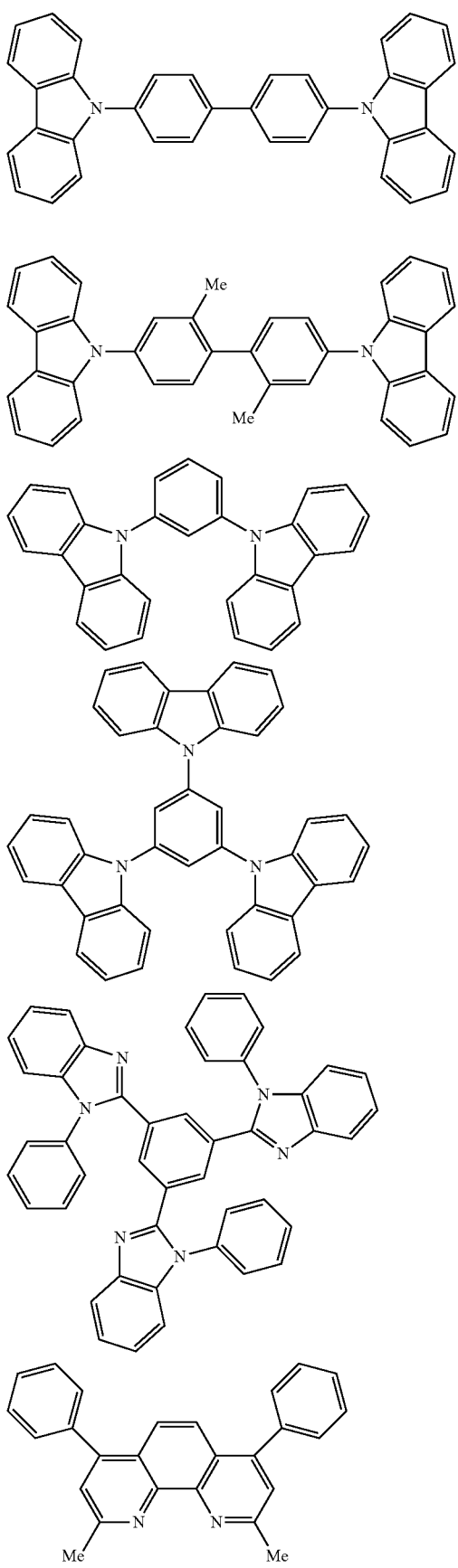
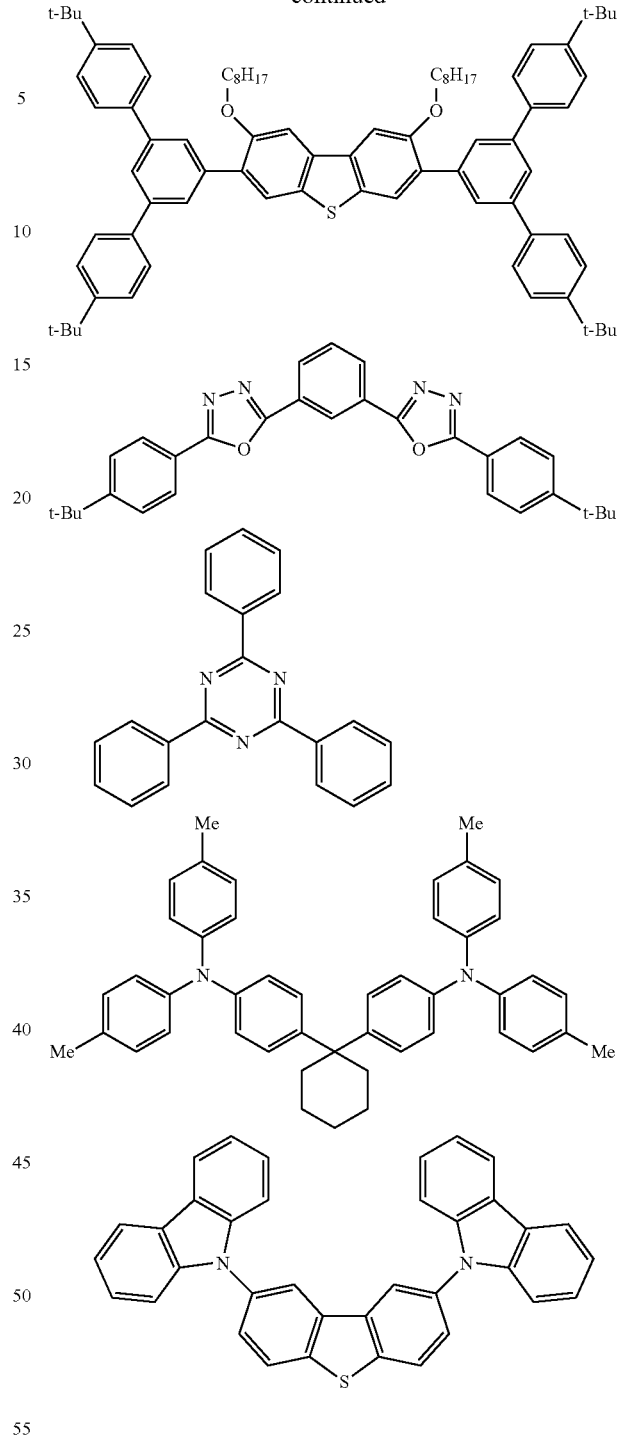

Examples of the polymer compound used for a host material (hereinafter referred to as "polymers host") include the polymer compounds described as hole transportation materials or electron transporting materials.

The light emitting layer may be a monolayer structure consisting of one or two or more of the light emitting materials, and may be a multilayer structure consisting of a plurality of layers having the same composition or different compositions.

The thickness of the light emitting layer is, for example, 5 nm to 1 μm.

[Electron Transporting Layer]

The electron transporting layer may be formed, for example, using one or two or more of the above-mentioned electron transporting compounds, and may be formed preferably using the composition of the present embodiment containing one or two or more of an above-mentioned electron transporting compounds.

The electron transporting layer may be a monolayer structure consisting of one or two or more of the electron transporting compounds, and may be a multilayer structure consisting of a plurality of layers having the same composition or different compositions.

The thickness of the electron transporting layer is, for example, 1 nm to 1 μm.

[Electron Injecting Layer]

The electron injecting layer may be formed, for example, using one or two or more of the above-mentioned electron injecting compounds, and may be formed preferably using the composition of the present embodiment containing one or two or more of the above-mentioned electron transporting compounds.

The electron injecting layer may be a monolayer structure consisting of one or two or more of the electron injecting compounds, and may be a multilayer structure consisting of a plurality of layers having the same composition or different compositions.

The thickness of the electron injecting layer is, for example, 1 nm to 1 μm.

[Anode]

Examples of the material of the anode may include conductive metal oxides and translucent metals. The anode material is preferably indium oxide, zinc oxide, or tin oxide; a conductive compound such as indium tin oxide (ITO) or indium zinc oxide; a complex of silver, palladium, and copper (APC); NESA, gold, platinum, silver, or copper.

The anode may be a monolayer structure consisting of one or two or more of these materials, and may be a multilayer structure consisting of a plurality of layers having the same composition or different compositions.

A known method can be used as a method for manufacturing an anode, and examples thereof include vacuum deposition, sputtering, ion plating, plating, and a method by forming a film from a solution (a mixed solution with a polymer binder may be used).

The thickness of the anode is, for example, 10 nm to 10 μm.

[Cathode]

Examples of the material of the cathode include metals such as lithium, sodium, potassium, rubidium, cesium, beryllium, magnesium, calcium, strontium, barium, aluminum, zinc, and indium; alloys of two or more of those metals; alloys of one or more of those metals with one or more of silver, copper, manganese, titanium, cobalt, nickel, tungsten, and tin; and graphite and graphite intercalation compounds. Examples of the alloys include a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy, a metal nanoparticle, a metal nanowire, and a conductive metal oxide nanoparticle.

A known method can be used as a method for manufacturing a cathode, and vacuum deposition, sputtering, ion plating, and a method by forming a film from a solution (a mixed solution with a polymer binder may be used) are illustrated. When the cathode is a metal nanoparticle, a metal nanowire, and a conductive metal oxide nanoparticle, the method by forming a film from a solution is used.

The thickness of the cathode is, for example, 1 to 1000 nm. The cathode may be a monolayer structure and may be formed as a multilayer structure.

[Other Components]

The light emitting device of the present embodiment may have a sealing member on the opposite side of the light emitting layer and the like to the substrate, and may have optional components for constituting a display device, such as filters including a color filter, a fluorescent conversion filter and the like, circuits and wirings, which are required for the drive of pixels, and the like besides.

[Manufacturing Method]

The light emitting device of the present embodiment can be manufactured, for example, by successively stacking layers on a substrate. Specifically, the light emitting device can be manufactured by providing an anode on a substrate, providing layers such as a hole injecting layer and a hole transporting layer thereon, providing a light emitting layer thereon, and providing layers such as an electron transporting layer and an electron injecting layer thereon, and further stacking a cathode thereon. As another manufacturing method, the light emitting device can be manufactured by providing a cathode on a substrate, and providing layers such as an electron injecting layer, an electron transporting layer, a light emitting layer, a hole transporting layer, and a hole injecting layer thereon, and further stacking an anode thereon. As yet another manufacturing method, manufacturing can be performed by opposing and joining an anode or an anode side substrate obtained by stacking layers on an anode; and a cathode or a cathode side substrate obtained by stacking layers on a cathode.

As described above, the composition of the present embodiment is suitable as a composition for light emitting devices (especially organic electroluminescent devices), and is particularly suitable as a composition for forming a hole injecting layer, a composition for forming a hole transporting layer, a composition for forming an electron transporting layer, or a composition for forming an electron injecting layer.

[Use]

The light emitting device of the present embodiment can be used suitably as displays in computers, television sets, mobile terminals and the like; planar light sources for backlights in liquid crystal displays; or planar illumination light sources, and can also be used as a curved light source and a curved display device when a flexible substrate is used.

EXAMPLES

The present invention will now be described in more detail by the following Examples, but the present invention is not limited to these Examples.

In the Examples, the polystyrene-equivalent number-average molecular weight (Mn) and the polystyrene-equivalent weight-average molecular weight (Mw) of the polymer compounds were determined by any one of the below size-exclusion chromatography (SEC) measurement conditions using tetrahydrofuran for the mobile phase.

<Measurement Conditions 1>

A polymer compound to measure was dissolved in tetrahydrofuran at a concentration of around 0.05% by weight, and 10 μL was injected into the SEC. The mobile phase was allowed to flow at a flow rate of 2.0 mL/min. As a column, a PLgel MIXED-B (manufactured by Polymer Laboratories Corporation) was used. A UV-VIS detector (manufactured by SHIMADZU CORPORATION, trade name: SPD-10Avp) was used as a detector.

<Measurement Conditions 2>

A polymer compound to measure was dissolved in tetrahydrofuran at a concentration of around 0.05% by weight, and 10 μL was injected into the SEC. The mobile phase was allowed to flow at a flow rate of 1.0 mL/min. As a column, a PLgel MIXED-B (manufactured by Polymer Laboratories Corporation) was used. A UV-VIS detector (manufactured by Tosoh Corporation, trade name: UV-8320GPC) was used as the detector.

NMR was measured by the following method.

A measurement sample of 5 to 10 mg was dissolved in about 0.5 mL of deuterated chloroform ($CDCl_3$), heavy tetrahydrofuran, heavy dimethyl sulfoxide, heavy acetone, heavy N,N-dimethylformamide, heavy toluene, heavy methanol, heavy ethanol, heavy 2-propanol, or heavy methylene chloride, and measured using an NMR apparatus (trade name: INOVA 300 or MERCURY 400 VX, manufactured by Agilent).

As an index of the purity of the compound, the value of the high-performance liquid chromatography (HPLC) area percentage was used. Unless specified otherwise, this value is the value at UV-254 nm in the HPLC apparatus (product name: LC-20A, manufactured by Shimadzu Corporation). At this time, the compound to be measured was dissolved in tetrahydrofuran or chloroform so as to have a concentration of 0.01 to 0.2% by weight, and 1 to 10 μL of the solution was injected into the HPLC apparatus in accordance with the concentration. For the HPLC mobile phase, the ratio of acetonitrile/tetrahydrofuran in the mixture was varied between 100/0 to 0/100 (volume ratio) while flowing at a flow rate of 1.0 mL/min. As the column, a Kaseisorb LC ODS 2000 (manufactured by Tokyo Chemical Industry) or an ODS column having equivalent performance was used. For the detector, a photodiode array detector (trade name: SPD-M20A, manufactured by Shimadzu Corporation) was used.

<Synthesis Example 1> Synthesis of Monomer CM1

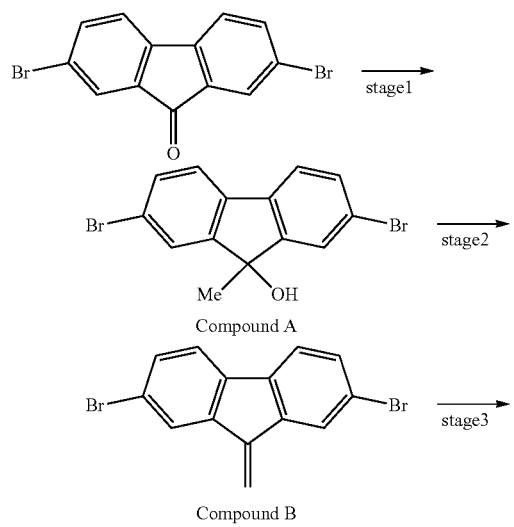

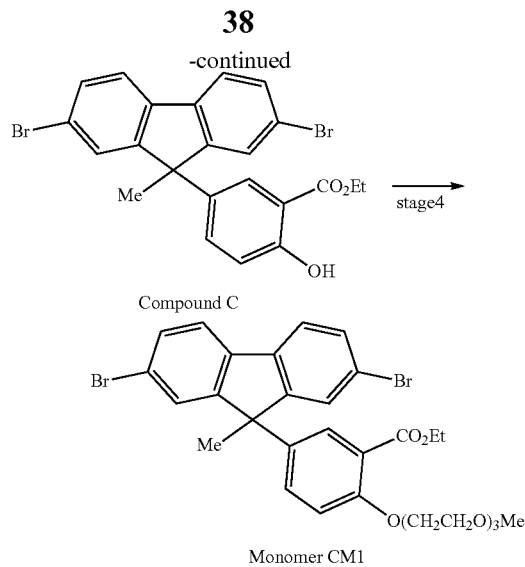

<Stage 1>

The atmosphere within a reaction vessel was replaced with a nitrogen gas atmosphere, then the reaction vessel was charged with 2,7-dibromo-9-fluorenone (92.0 g) and diethyl ether (3.7 L), and the mixture was cooled to 0° C. After 1 mol/L methylmagnesium iodide-diethyl ether solution (0.50 L) was dropped thereinto, the mixture was stirred at 0° C. for 3 hours.

The obtained reaction mixture was washed with an ammonium chloride solution, and the obtained organic layer was then dried over anhydrous sodium sulfate. Then, a crude product was obtained by filtering and concentrating the liquid under reduced pressure. A compound A (92.8 g) was obtained by purifying this crude product by silica gel column chromatography and then drying it under reduced pressure.

<Stage 2>

The atmosphere within a reaction vessel was replaced with a nitrogen gas atmosphere, then the reaction vessel was charged with the compound A (83.0 g), p-toluenesulfonic acid monohydrate (4.49 g) and chloroform (2.5 L), and the mixture was stirred under reflux for 1 hour. The obtained reaction mixture was washed with an ammonium chloride solution, and the obtained organic layer was then dried over anhydrous sodium sulfate. Then, a compound B (73.6 g) was obtained by filtering and concentrating the liquid under reduced pressure.

<Stage 3>

The atmosphere within a reaction vessel was replaced with a nitrogen gas atmosphere, then the reaction vessel was charged with the compound B (70.0 g), ethyl salicylate (104 g), mercaptoacetic acid (4.20 g) and methanesulfonic acid (1210 g), and the mixture was stirred at 70° C. for 8 hours. A crude product was obtained by dropping the obtained reaction mixture on ice water, filtering out the deposited solid and washing the obtained solid with methanol. A compound C (52.1 g) was obtained by purifying this crude product by silica gel column chromatography and then drying it under reduced pressure.

<Stage 4>

The atmosphere within a reaction vessel was replaced with a nitrogen gas atmosphere, then the reaction vessel was charged with the compound C (41.2 g), 2-[2-(2-methoxyethoxy)ethoxy]-ethyl-p-toluenesulfonate (75.8 g), N,N-dimethylformamide (214 g), potassium carbonate (54.4 g) and 1,4,7,10,13,16-hexaoxacyclooctadecane (4.68 g), and the mixture was stirred at 105° C. for 2 hours.

Water was added to the obtained reaction mixture, followed by extraction with ethyl acetate. The obtained organic layer was dried over anhydrous sodium sulfate. Then, a crude product was obtained by filtering and concentrating the filtrate under reduced pressure. A monomer CM1 (40.2 g, yield 76%) was obtained by purifying this crude product by silica gel column chromatography and then drying it under reduced pressure.

The NMR measurement result of the monomer CM is shown below. $^1$H-NMR (400 MHz, CDCl$_3$): δ (ppm) 1.37 (3H), 1.84 (3H), 3.36 (3H), 3.53 (2H), 3.58-3.79 (6H), 3.73 (2H), 4.12 (2H), 4.34 (2H), 6.80 (1H), 6.90 (1H), 7.28 (2H), 7.48 (2H), 7.58 (2H), 7.70 (1H).

<Synthesis Example 2> Synthesis of Monomer CM2

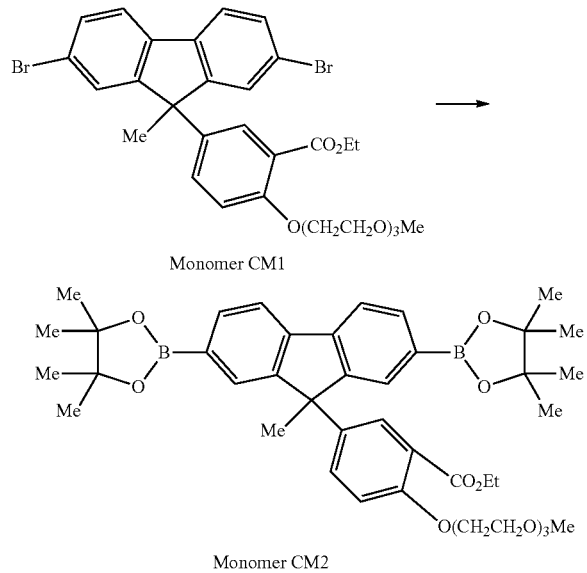

The atmosphere within a reaction vessel was replaced with a nitrogen gas atmosphere, then the reaction vessel was charged with the monomer CM1 (28.4 g), bis(pinacolato) diboron (24.30 g), [1,1'-bis(diphenylphosphino)ferrocene] palladium(II) dichloride dichloromethane adduct (0.35 g), 1,1'-bis(diphenylphosphino)ferrocene (0.24 g), potassium acetate (25.6 g) and 1,4-dioxane (480 mL), and the mixture was stirred at 120° C. for 17 hours.

A crude product was obtained by filtering the obtained reaction mixture and concentrating the filtrate under reduced pressure. A monomer CM2 (18.2 g, yield 56%) was obtained by purifying this crude product by silica gel column chromatography and crystallization sequentially and then drying it under reduced pressure.

The NMR measurement result of the monomer CM2 is shown below. $^1$H-NMR (400 MHz, CDCl$_3$): δ (ppm) 1.30-1.47 (27H), 1.88 (3H), 3.35 (3H), 3.53 (2H), 3.60-3.69 (4H), 3.73 (2H), 3.84 (2H), 4.10 (2H), 4.34 (2H), 6.74 (1H), 6.87 (1H), 7.58 (2H), 7.72-7.89 (5H).

<Synthesis Example 3> Synthesis of Monomers CM3 to CM6

Monomers CM3 to CM6 were synthesized according to methods which were described in the following literature, and monomers CM3 to CM6 exhibiting HPLC area percentage values of 99.5% or more were used.

The monomers CM3 to CM5 were synthesized according to a method of International Publication No. WO 2013/146806.

The monomer CM6 was synthesized according to a method of International Publication No. WO 2009/157424.

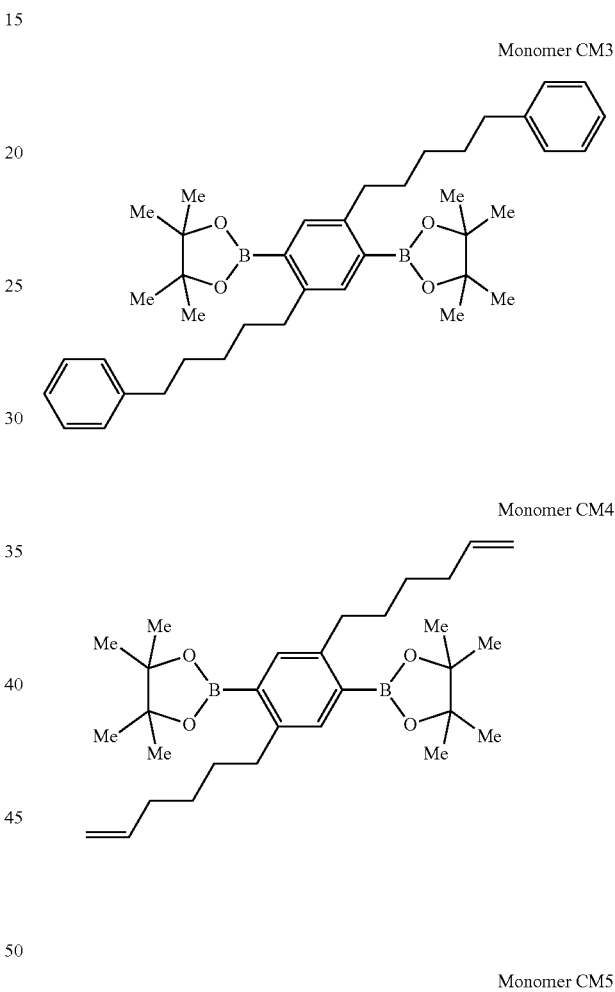

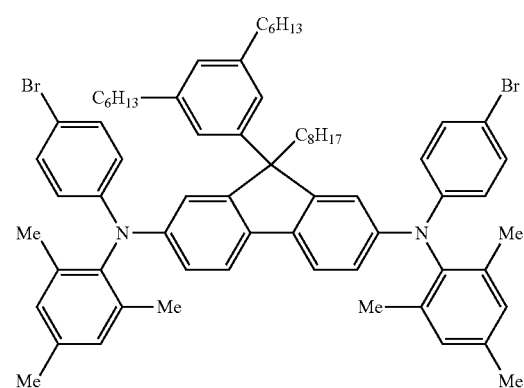

-continued

Monomer CM6

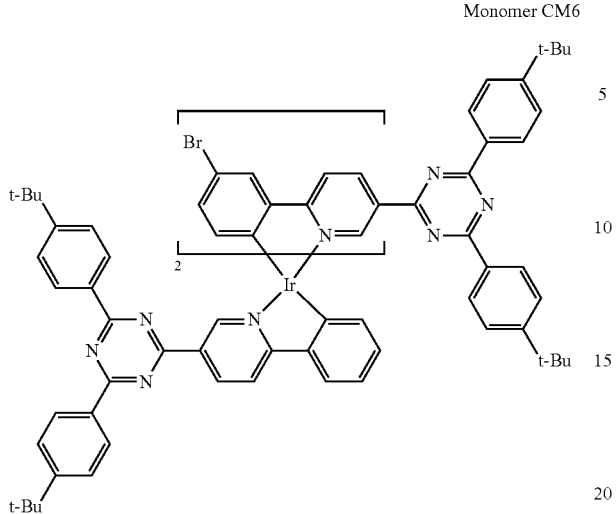

<Synthesis Example 4> Synthesis of Polymer Compound 2

(Step 1)
The atmosphere within a reaction vessel was replaced with an argon gas atmosphere, then the reaction vessel was charged with a monomer mixture 1a (13.8 g, monomer CM1:monomer CM2=50:50 (molar ratio)), dichlorobis(triphenylphosphine)palladium (0.6 mg), tetrabutylammonium bromide (6 mg), toluene (6 mL) and an aqueous 2 mol/L sodium carbonate solution (2 mL), the temperature of an oil bath was adjusted to 100° C., and the mixture was stirred under reflux for 6 hours.

(Step 2)
Phenylboronic acid (35 mg) was added to the obtained reaction solution, the temperature of the oil bath was adjusted to 100° C., and the mixture was stirred under reflux for 14 hours.

(Step 3)
An aqueous sodium diethyldithiocarbamate solution was added to the obtained reaction solution, and the mixture was stirred at 80° C. for 2 hours. When the obtained reaction solution was dropped into methanol, a precipitation formed. A solid was obtained by filtering out and drying the obtained precipitate. This solid was dissolved in chloroform and purified by passing through an alumina column and a silica gel column in that order. When the obtained solution was dropped into methanol and the mixture was stirred, a precipitation formed. A polymer compound 1 (0.57 g) was obtained by filtering out this precipitation and drying it. The Mn of the polymer compound 1 measured according to the measurement conditions 2 was $2.0 \times 10^4$, and the Mw was $4.3 \times 10^4$.

(Step 4)
The atmosphere within a reaction vessel was replaced with an argon gas atmosphere, then the reaction vessel was charged with the polymer compound 1 (0.20 g), tetrahydrofuran (18 mL), methanol (9 mL), cesium hydroxide monohydrate (97 mg), and water (1 mL), and the mixture was stirred at 65° C. for 2 hours. Methanol (52 mL) was added thereto, and the mixture was stirred at 65° C. for 6 hours.

(Step 5)
A solid was obtained by concentrating the obtained reaction solution under reduced pressure. This solid was dissolved in methanol, followed by filtration. When the filtrate was dropped into isopropanol and the mixture was stirred, a precipitate formed. A polymer compound 2 (0.20 g) was obtained by filtering out this precipitate and drying it.

The polymer compound 2 is a polymer consisting of a constitutional unit represented by the following formula (A) on the basis of a theoretical value calculated from the amount of the fed raw material.

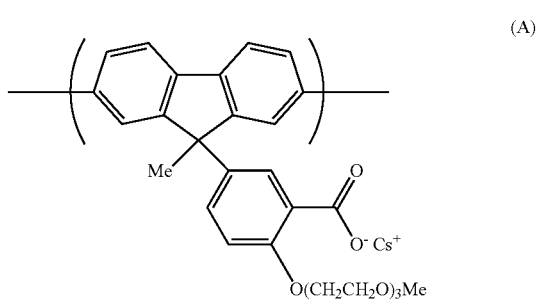

(A)

<Synthesis Example 5> Synthesis of Polymer Compound 3

(Step 1)
The atmosphere within a reaction vessel was replaced with an inert gas atmosphere, then the reaction vessel was charged with the monomer CM3 (2.52 g), the monomer CM4 (0.47 g), the monomer CM5 (4.90 g), the monomer CM6 (0.53 g) and toluene (158 mL), and the mixture was heated to 95° C.

(Step 2)
To the reaction solution were added an aqueous 20% by weight tetraethylammonium hydroxide solution (16 mL) and dichlorobis(tris-o-methoxyphenylphosphine)palladium (4.2 mg), and the mixture was refluxed for 8 hours.

(Step 3)
After the reaction, phenylboronic acid (0.12 g), an aqueous 20% by weight tetraethylammonium hydroxide solution (16 mL), and dichlorobis(tris-o-methoxyphenyl phosphine) palladium (4.2 mg) were added thereto, and the mixture was refluxed for 15 hours.

(Step 4)
Then, an aqueous sodium diethyldithiocarbamate solution was added thereto, and the mixture was stirred at 85° C. for 2 hours. When the reaction solution was washed with an aqueous 3.6% by weight hydrochloric acid solution twice, an aqueous 2.5% by weight ammonia solution twice, and water 4 times after cooling and the obtained solution was dropped into methanol, a precipitate formed. The precipitate was dissolved in toluene and purified by passing through an alumina column and a silica gel column in that order. The obtained solution was dropped into methanol, followed by stirring the mixture, and a polymer compound 3 (6.02 g) was obtained by filtering out the obtained precipitation and drying it. The Mn of polymer compound 3 measured according to the measurement conditions 1 was $3.8 \times 10^4$, and Mw was $4.5 \times 10^5$.

The polymer compound 3 was a copolymer comprising a constitutional unit derived from the monomer CM3, a constitutional unit derived from the monomer CM4, a constitutional unit derived from the monomer CM5, and a constitutional unit derived from the monomer CM6 at a molar ratio of 40:10:47:3 on the basis of a theoretical value calculated from the amount of the fed raw material.

<Synthesis Example 6> Synthesis of Phosphorescent Compounds 1 and 2

Phosphorescent compounds 1 and 2 were synthesized according to methods which were described in the following literature, and phosphorescent compounds 1 and 2 exhibiting HPLC area percentage values of 99.5% or more were used.

The phosphorescent compound 1 was synthesized on the basis of a method of International Publication No. WO 2006/121811.

The phosphorescent compound 2 was synthesized according to a method of International Publication No. WO 2009/131255.

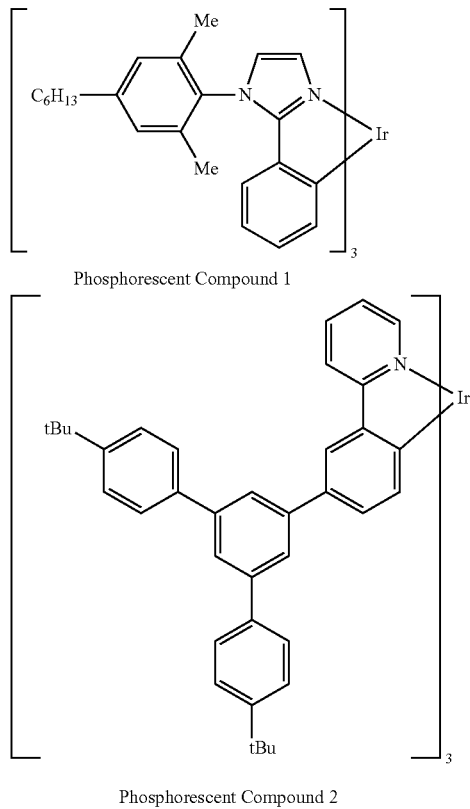

Phosphorescent Compound 1

Phosphorescent Compound 2

In Example and Comparative Example, fluorinated alcohols F-alc 1 to 7 shown in Table 1 were used. The amounts of hydrogen fluoride which is generated from the fluorinated alcohols are shown together in Table 1. The F-alc 3 to 7 were obtained by mixing the F-alc 1 and 2 at ratios shown in Table 1. The method for measuring the amounts of hydrogen fluoride which were generated from the fluorinated alcohols is as follows (also see FIG. 1 together).

A 2 L round bottom flask 2 equipped with a balloon 1 (volume: around 1000 mL) was charged with 5 mL of a fluorinated alcohol 3, and a magnetic stirring bar 4 was placed therein. At this time, the balloon 1 was inflated to such a degree that the pressure was around atmospheric pressure in the round bottom flask 2. The fluorinated alcohol 3 was airtightly stirred at 25° C. for 1 hour. After stirring, gas in the round bottom flask was injected into a hydrogen fluoride detector tube (manufactured by GASTEC CORPORATION) through a Teflon (registered trademark) tube using a gas collector 5 (manufactured by GASTEC CORPORATION, trade name: GV-100S), and the volume of hydrogen fluoride on the basis of the volume of the injected gas was read from the detector tube and defined as the amount of hydrogen fluoride (ppm by volume).

TABLE 1

|  | Fluorinated alcohol | Amount of hydrogen fluoride (ppm by volume) |
| --- | --- | --- |
| F-alc 1 | 1H,1H,5H-Octafluoropentanol | 0 |
| F-alc 2 | 1H,1H,5H-Octafluoropentanol | 90 |
| F-alc 3 | F-alc 1 + F-alc 2 (Weight ratio 92/8) | 0.05 |
| F-alc 4 | F-alc 1 + F-alc 2 (Weight ratio 90/10) | 0.3 |
| F-alc 5 | F-alc 1 + F-alc 2 (Weight ratio 85/15) | 1.0 |
| F-alc 6 | F-alc 1 + F-alc 2 (Weight ratio 75/25) | 5.0 |
| F-alc 7 | F-alc 1 + F-alc 2 (Weight ratio 50/50) | 20 |

<Example 1> Manufacturing of Light Emitting Device D1

(Formation of Anode and Hole Injecting Layer)

An anode was formed by attaching an ITO film to a glass substrate to a thickness of 45 nm by sputtering. A film of a hole injecting material ND-3202 produced by Nissan Chemical Industries, Ltd. was formed on the anode to a thickness of 35 nm by spin coating, heated at 50° C. for 3 minutes on a hot plate in an air environment from which ozone was removed to volatilize solvent, and successively heated on the hot plate at 240° C. for 15 minutes to form a hole injecting layer.

(Formation of Hole Transporting Layer)

The polymer compound 3 was dissolved in xylene at a concentration of 0.65% by weight. A film was formed on the hole injecting layer to a thickness of 20 nm by spin coating using the obtained xylene solution, and a hole transporting layer was formed by heating on the hot plate at 180° C. for 60 minutes under a nitrogen gas atmosphere.

(Formation of Light Emitting Layer)

The low molecular weight compound 1 (LT-N4013 produced by Luminescence Technology Corp.) represented by the following formula,

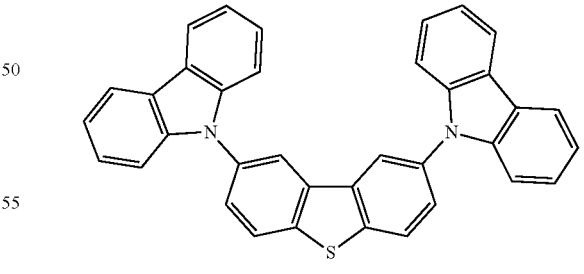

Low Molecular Weight Compound 1 the phosphorescent compound 1 and the phosphorescent compound 2 (weight ratio: low molecular weight compound 1/phosphorescent compound 1/phosphorescent compound 2=74/25/1) were dissolved in toluene at a concentration of 2.0% by weight to prepare a toluene solution. A film was formed on the hole transporting layer to a thickness of 75 nm by spin coating using this toluene solution, and the light emitting layer was formed by heating at 130° C. for 10 minutes under a nitrogen gas atmosphere.

(Formation of Electron Transporting Layer)

The polymer compound 2 was dissolved in the F-alc 1 at a concentration of 0.25% by weight to prepare a F-alc 1 solution. A film was formed on the light emitting layer to a thickness of 10 nm by spin coating using this F-alc 1 solution, and an electron transporting layer was formed by heating at 130° C. for 10 minutes under a nitrogen gas atmosphere.

(Formation of Cathode and Electron Injecting Layer)

The substrate on which the electron transporting layer was formed was placed in a vapor deposition machine, followed by decompression to $1.0 \times 10^{-4}$ Pa or less, and sodium fluoride was then evaporatively deposited on the electron transporting layer to around 4 nm as a cathode, and aluminum was next evaporatively deposited to around 100 nm thereon. A light emitting device D1 was manufactured by then sealing using a glass substrate.

<Examples 2 to 5 and Comparative Example 1 to 2> Manufacturing of Light Emitting Devices D2 to D5 and CD1 to CD2

Light emitting devices D2 to D5 and CD1 to CD2 were manufactured in the same way as in Example 1 except that fluorinated alcohols shown in Table 2 instead of the F-alc 1 were used.

Figure 2:
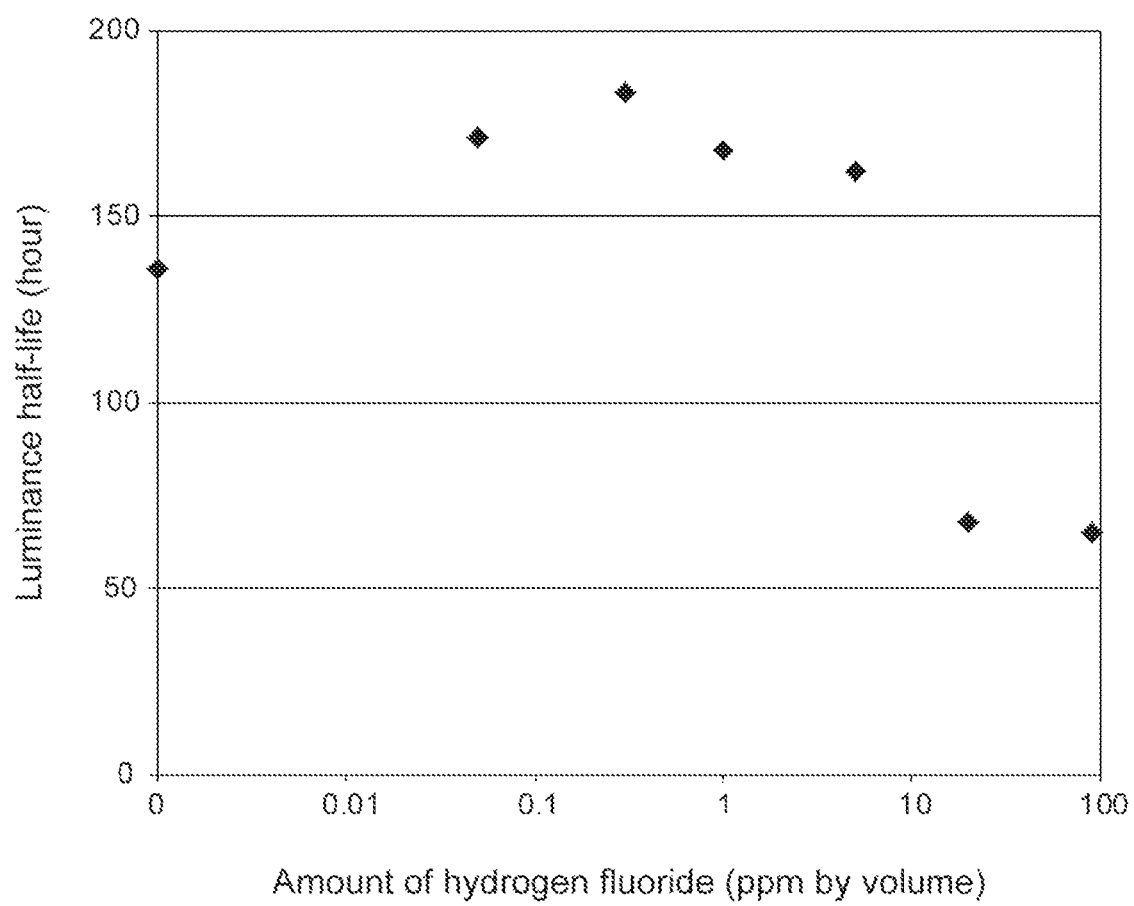
FIG. 2 is a graph showing the relationship between the amounts of hydrogen fluoride from fluorinated alcohols and the luminance half-lives of light emitting devices in Examples and Comparative Examples.

As to light emitting devices D1 to D5 and CD1 to CD2, luminance half-lives were measured by defining 6000 cd/m² as the initial luminance. The results are shown in Table 2. The graph illustrating the relationship between the amounts of hydrogen fluoride of the fluorinated alcohols used in Examples and Comparative Examples and the luminance half-lives of light emitting devices by plotting semilogarithmically is shown in FIG. 2. Furthermore, the case where the amount of hydrogen fluoride was 0 ppm by volume (Example 1) was also shown in the graph for convenience.

TABLE 2

|  | Light emitting device | Fluorinated alcohol (amount of hydrogen fluoride) | Luminance half-life (hour) |
|---|---|---|---|
| Example 1 | D1 | F-alc 1 (0 ppm by volume) | 136 |
| Example 2 | D2 | F-alc 3 (0.05 ppm by volume) | 171 |
| Example 3 | D3 | F-alc 4 (0.3 ppm by volume) | 183 |
| Example 4 | D4 | F-alc 5 (1.0 ppm by volume) | 168 |
| Example 5 | D5 | F-alc 6 (5.0 ppm by volume) | 162 |
| Comparative Example 1 | CD1 | F-alc 7 (20 ppm by volume) | 68 |
| Comparative Example 2 | CD2 | F-alc 2 (90 ppm by volume) | 65 |

As is seen from Table 2 and FIG. 2, the light emitting devices manufactured using compositions of the present invention are more excellent in the lifetime than the light emitting devices not using compositions of the present invention.

REFERENCE SIGNS LIST

1: balloon, 2: round bottom flask, 3: fluorinated alcohol, 4: magnetic stirring bar, 5: gas collector.

The invention claimed is:

1. A composition comprising:
   a fluorinated alcohol represented by the following formula (1):

$$C_{nF}H_{2nF+1-mF}F_{mF}OH \qquad (1)$$

wherein nF and mF are each independently an integer being 1 or more and satisfying 2 nF+1≤mF; and
   a charge transporting compound,
   wherein an amount of hydrogen fluoride generated from the fluorinated alcohol under atmospheric pressure at 25° C. is 0.01 ppm by volume or more and 5.0 ppm by volume or less.

2. The composition according to claim 1, wherein the fluorinated alcohol is a primary alcohol.

3. The composition according to claim 1, wherein the charge transporting compound is at least one selected from the group consisting of aromatic hydrocarbon compounds; aromatic heterocyclic compounds; organosilane compounds; alkali metal salts and alkaline earth metals salts thereof; halides, oxide salts, and carbonates of alkaline metals and alkaline earth metals; and metal complexes.

4. The composition according to claim 1, wherein the charge transporting compound is at least one selected from the group consisting of aromatic hydrocarbon compounds and aromatic heterocyclic compounds.

5. The composition according to claim 1, wherein the charge transporting compound is at least one selected from the group consisting of alkali metal salts and alkaline earth metal salts of aromatic hydrocarbon compounds; and alkali metal salts and alkaline earth metal salts of aromatic heterocyclic compounds.

6. A method for manufacturing a light emitting device comprising an anode, a cathode, and at least one layer selected from the group consisting of a hole injecting layer, a hole transporting layer, an electron injecting layer and an electron transporting layer,
   the method comprising forming the layer by applying a composition comprising:
   a fluorinated alcohol represented by the following formula (1):

$$C_{nF}H_{2nF+1-mF}F_{mF}OH \qquad (1)$$

wherein nF and mF are each independently an integer being 1 or more and satisfying 2 nF+1≤mF; and
   a charge transporting compound,
   wherein an amount of hydrogen fluoride generated from the fluorinated alcohol under atmospheric pressure at 25° C. is 0.01 ppm by volume or more and 5.0 ppm by volume or less.

7. The method according to claim 6, wherein the fluorinated alcohol is a primary alcohol.

8. The method according to claim 6, wherein the charge transporting compound is at least one selected from the group consisting of aromatic hydrocarbon compounds; aromatic heterocyclic compounds; organosilane compounds; alkali metal salts and alkaline earth metals salts thereof; halides, oxide salts, and carbonates of alkaline metals and alkaline earth metals; and metal complexes.

9. The method according to claim 6, wherein the charge transporting compound is at least one selected from the group consisting of aromatic hydrocarbon compounds and aromatic heterocyclic compounds.

10. The method according to claim 6, wherein the charge transporting compound is at least one selected from the group consisting of alkali metal salts and alkaline earth metal salts of aromatic hydrocarbon compounds; and alkali metal salts and alkaline earth metal salts of aromatic heterocyclic compounds.

* * * * *